US007439233B1

(12) United States Patent
Yoo

(10) Patent No.: US 7,439,233 B1
(45) Date of Patent: Oct. 21, 2008

(54) VACCINE FOR HOUSE DUST MITE ALLERGEN USING NAKED DNA

(76) Inventor: Tai June Yoo, 7328 Cotton Plant Cove, Memphis, TN (US) 38119

( * ) Notice: Subject to any disclaimer, the term of this patent is extended or adjusted under 35 U.S.C. 154(b) by 0 days.

(21) Appl. No.: 09/513,645

(22) Filed: Feb. 25, 2000

Related U.S. Application Data

(60) Provisional application No. 60/121,547, filed on Feb. 25, 1999.

(51) Int. Cl.
*A01N 43/04* (2006.01)
*A01N 63/00* (2006.01)
*A61K 31/715* (2006.01)
*A61K 48/00* (2006.01)

(52) U.S. Cl. ..................... 514/44; 424/93.21
(58) Field of Classification Search .............. 424/184.1, 424/275.1, 536, 93.21; 514/44; 536/23.1; 435/320.1
See application file for complete search history.

(56) References Cited

U.S. PATENT DOCUMENTS

| 5,508,386 | A | * | 4/1996 | Zanetti et al. | ............ | 530/387.3 |
| 5,958,891 | A | * | 9/1999 | Hsu et al. | ...................... | 514/44 |
| 6,077,517 | A | * | 6/2000 | Thomas et al. | ........... | 424/275.1 |
| 6,121,247 | A | | 9/2000 | Huang et al. | | |
| 6,147,201 | A | * | 11/2000 | Thomas et al. | ............. | 536/23.2 |
| 6,268,491 | B1 | * | 7/2001 | Garman et al. | ............. | 536/23.5 |

FOREIGN PATENT DOCUMENTS

| EP | 0123456 | A2 * | 1/2000 | ................. | 100/100 |
| WO | 9424281 | | 10/1994 | | |

OTHER PUBLICATIONS

Verma, I.M. et al. Gene therapy-promises, problems and prospects, Nature, vol. 389, 1997, pp. 239-242.*
Orkin, S.H. Report and Recommendations of the Panel to asssess the NIH investment in research on gene therapy, Dec. 1995.*
Smith et al. Comparative analysis of the genes encoding group 3 allergens from *Dermatophagoides pteronyssinus* and *Dermatophagoides farinae* pp. 133-140 1996.*
Kwon et al. Immunoprotective effect of vaccination with DNA encoding T cell epitopes on the Der p induced IgE production pp. S110 vol. 103No. 1 1999.*
Hetzel et al. An epitode delivery system for use with recombinant mycobacteria vol. 66, No. 8 1998.*
Nacksung et al. Tl suppressive vaccination of allergen-inducecd immunoglobulin E production by the naked DNA vaccine vol. 101,No. 1 1998.*
Kwon et al. The effect of vaccination with DNA encoding murine T-cell epitopes on the Der p 1 and 2 induced immunoglobin E synthesis pp. 741-748 2001.*
Nishiyama et al. Tl cloning and expression in *Escherichia coli* of cDNA encoding house dust mite allergen Der f 3, serine protease from *Dermathphagoides farinae*. pp. 62-66 1995.*
Garbe, Microbiology, 1994, vol. 140, p. 133-138.*

XP-000916359, "Immunoprotective Effect of Vaccination with DNA Encoding T cell Epitopes on the Der p Induced IgE Production," by Yoo et al.
XP-000652250, "Preferential induction of a Th 1 immune response and inhibition of specific IgE antibody formation by plasmid DNA immunization," by Raz et al., published in Proc. Natl Acad. Sci. USA, vol. 93, pp. 5141-5145, May 1996.
XP-000915972, "Immunoprophylaxis of allergen-induced immunoglobulin E synthesis and airway hyperresponsiveness in vivo by genetic imunization," by Hsu et al., published in Nature Medicine, vol. 2, No. 5, May 1996.
D. Broide et al., "Intradermal Gene Vaccination Down-Regulates Both Arms of the Allergic Response" (1997) J. Allergy Clin. Immunol. vol. 99, No. 1, part 2, p. S129.
McDonnell et al., "Immunization" (1997) vol. 278, No. 22, pp. 2000-2006.
Van Uden and Raz, "Immunostimulatory DNA and Applications to Allergic Disease" (1999) J. Allergy Clin. Immunol. vol. 104, pp. 902-910.
L. Lichtenstein, "Allergic-ISS Conjugates, A Novel Modality of Immunotherapy" (Mar. 2000) Annual American Academy of Allergy, Asthma, & Immunology Meeting, San Diego, CA.
D. Umetsu, "Induction of Protective Immunity in Asthma by Genetic Vaccination: The Role of T-Cell Subsets that Reverse Airway Hyperreactivity" (Mar. 2000) Annual American Academy of Allergy, Asthma, & Immunology Meeting, San Diego, CA.
Platts-Mill, T.A.E. et al., "Dust mites: Immunology, allergic disease, and environmental control", *J. Allergy Clin. Immunol.* 1987, vol. 80, pp. 755-775.
WHO Bulletin "Dust mites allergens and asthma: a world wide problem", 1988, vol. 66, pp. 769-780.
Ulmer, J.B., et al. "Heterologous protection against influenza by infection of DNA encoding a viral protein", *Science*, 1993, vol. 259, pp. 1745-1749.
Wang, B., et al., "Gene inoculation generates immune responses against human immunodeficienty virus type 1", *Proc. Natl. Acad. Sci.*, 1993, vol. 90, pp. 4156-4160.
Raz, E., et al. "Intradermal gene immunization: The possible role of DNA uptake in the induction of cellular immunity to viruses", *Proc. Natl., Acad. Sci.*, 1994, vol. 91, pp. 9519-9523.
Wolff, J.A., et al., "Long persistence of plasmid DNA and foreign gene expression in mouse muscle", *Hum. Mol. Gen.*, 1992, pp. 363-369.
Slater, J.E., et al., "DNA vaccine inhibits IgE responses to the latex allergen Hev b 5 in mice", *J. Allergy Clin. Immunol.*, 1997, vol. 99, p. 504.
Cheng, K.C., et al., "House dust mite-induced sensitivity in mice", *J. Allergy Clin. Immunol.*, 1998, vol. 101, pp. 51-59.
Enander, I., "Mononuclear cells, mast cells and mucous cells as part of the delayed hypersensitivity response to aerosolized antigen in mice", *Immunol.*, 1984, vol. 51, pp. 661-668.
Hessel, E.M., "Bronchoconstriction and airway hyperresponsiveness after ovalbumin inhalation in sensitized mice", *J. Phamac., Enviro. Toxicology and Phamac.*, 1995, Section 293, pp. 401-412.

(Continued)

*Primary Examiner*—Michael C. Wilson
(74) *Attorney, Agent, or Firm*—Foley & Lardner LLP

(57) ABSTRACT

Vaccination with the DNA encoding T-cell epitopes to the house dust mite *Dermatophagoides pteronyssinus* (Der p) and *Dermatophagoides farinae* (Der f were effective in the inhibition of the allergen induced IgE synthesis. Gene therapy using T-cell epitope encoding DNA is useful in combating allergic disease.

8 Claims, 18 Drawing Sheets

OTHER PUBLICATIONS

Droste, J.-H., et al., "Association of skin test reactivity, specific IgE, total IgE, and eosinophils with nasal symptoms in a community-based population study", *J. Allergy Clin. Immunol.*, 1996, vol. 97, pp. 922-932.

Yssel, H., et al., "T cell activation-inducing epitopes of the house dust mite allergen, Proliferation and lymphokine production patterns by Der p 1-specific CD+4 T-cell clones", *J. Immunol.*, 1992, vol. 148, pp. 738-745.

Higgins, J.A. et al., "Peptide-induced nonresponsiveness of HLA-DP restricted human T cells reactive with *Dermatophagiodes* spp. (house dust mite)", *J. Allergy Clin. Immunol.*, 1992, vol. 90, pp. 749-756.

Bot, A. et al., "Kinetics of generation and persistence on membrane class II molecules of a viral peptide expressed on foreign and self proteins", *J. Immunol.* 1996, 157(8), pp. 3436-3442.

Demotz, S. et al., "The minimal number of class II MHC-antigen complexes needed for T cell activiation", *Science*, 1990, pp. 1028-1030.

Van der Zee, J.S. et al., "Skin tests and histamine release with P1-depleted *Dermatophagoides pteronyssinus* body extracts and purified P1", *J. Allergy Clin. Immunol.*, 1988 vol. 81, pp. 884-896.

Lin, K. L. et al., "Allergens, IgE Mediators, inflammatory mechanisms. Characterizations of Der p 5 allergen, cDNA analysis, and IgeE-mediated reactivity to the recombinant protein", *J. Allergy Clin. Immunol.*, 1994, pp. 989-996.

Singer, G.G. et al., "The Fas antigen is involved in peripheral but not thymic deletion of T lymphocytes in T cell receptor transgenic mice", *Immunity*, 1994, pp. 365-371.

Chen, Y. et al., "Peripheral deletion of antigen-reactive T cells in oral tolerance", *Nature*, 1995, pp. 177-180.

Tighe, H. et al., "Gene vaccination: plasmid DNA is more than just a blueprint", *Immunol.*, 1998, pp. 89-97.

Mosmann, T.R., et al., "TH1 and TH2 cells: different patterns of lymphokine secretion lead to different functional properties", *Annu. Rev. Immunol.*, 1989, pp. 145-173.

Finkelman, F.D. et al., "IL-4 required to generate and sustaine in vivo IgE responses", *J. Immunol.*, 1988, pp. 2335-2341.

Snapper, C.M. et al., "Interferon-γ and B cell stimulatory factor-1 reciprocally regulate Ig isotype production", *Science* 1987, pp. 944-947.

Lee, D.J. et al., "Inhibition of IgE antibody formation by plasmid DNA immunization is mediated by both and CD8+ T cells", *Int. Arch. Allergy Immunol.*, 1997, pp. 227-230.

Coffman, R.L. et al., "B Cell stimulatory factor-1 enhances the IgE response of lipopolysaccharide-activated B cells", *J. Immunol.*, 1986, pp. 4538-4541.

Krug N., et al., "How do lymphocytes get into the asthmatic airways? Lymphocyte traffic into and within the lung in asthma", *Clini Experi Allergy*, 1998, pp. 10-18.

Ying, S. et al., Phenotype of cells expressing mRNA for Th2-type(interleukin 4 and interleukin 5) and Th 1 type(interleukin 2 and interferon) cytyokines in bronhoalveolar lavage and brochial biopsies from atopic asthmatic and normal control subjects, *Am J. Respir Cell Mol. Biol.*, 1995, pp. 477-487.

Humbert M. et al., "IL-4 and IL-5 mRNA and protein in bronchial biopsies from patients with atopic and nonatopic astham: evidence against 'intricnsic' astham being a distinct immunopathologic entity", *Am J Respir Crit Care Med.*, 1996, pp. 1497-1504.

Hsieh, K. H. et al., "Changes of lymphoproliferative responses of T cell subsets to allergen and mitogen after hyposensitization in asthmatic children", *J. Allergy Clin. Immunol.*, 1984, pp. 34-40.

Ulmer, Jeffrey B et al., "DNA Vaccines", *Imm. to Infection*, pp. 531-536.

O'Hehir R.E., et al., "House dust mite allergy: from T-cell epitopes to immunotherapy", *Jr. of Clin. Invest.*, (1993), pp. 763-772.

Johnston S.A. et al., "Gene Gun Transfection of Animal Cells and Genetic Immunization", *Methods in Cell Biology*, vol. 43, pp. 353-365.

Benn, S.I. et al., "Particle-mediated Gene Transfer with Transforming Growth Factor—1 cDNAs Enhances Wound Repair in Rat Skin", *Jrn. Clin. Invest.*, vol. 98, No. 12, (1996), pp. 2894-2902.

Krieg, A. M. et al., "CpG motifs in bacterial DNA trigger direct B-cell activation", *Nature*, vol. 374 (1995) pp. 546-549.

Hoffman S. L. et al., "Protection against malaria by immunization with a Plasmodium yoelii circumsporozoite protein nucleic acid vaccine".

Ulmer J. B., "Heterologous Protection Against Influenza by Injection of DNA Encoding a Viral Protein", *Science*, vol. 259 (March), pp. 1745-1749.

Den Hurk et al., "Strategies for Improved Formulation and Delivery of DNA Vaccines to Veterinary Target Species", *Immunol Rev.*, vol. 199, pp. 113-125, 2004.

McCluskie et al., "Route and Method of Delivery of DNA Vaccine Influence Immune Responses in Mice and Non-Human Primates", *Mol. Med.*, vol. 5, pp. 287-300, 1999.

Pomes et al., "Novel Allergen Structures with Tandem Amino Acid Repeats Derived from German and American Cockroach", *Journal of Biological Chemistry*, vol. 237, No. 46, pp. 30801-30807, 1998.

Promega Corporation, Technical Bulletin 215, pp. 1-13, dated Jun. 2000.

Rosenberg et al., "Inability to Immunize Patients with Metastatic Melanoma Using Plasmid DNA Encoding the gp100 Melanoma-Melanocyte Antigen", *Human Gene Therapy*, vol. 14, pp. 709-714, May 20, 2003.

Scheerlinck et al., "Genetic Adjuvants for DNA Vaccines", *Vaccine*, vol. 19, pp. 2647-2656, 2001.

* cited by examiner

```
                           SEQUENCE LISTING

<160> NUMBER OF SEQ ID NOS: 84

<210> SEQ ID NO 1
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccggaattcg ccgccaccat gactgtcact cccattcgta tgc                    43

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgctctagat taagccaaat aagctgattc agttgc                            36

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 3
ccggaattcg ccgccaccat gcgtggtatt gaatacatcc aacat                45

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgctctagat tattctcgtg caacgtatcg atagta                          36

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccggaattcg ccgccaccat gcgtttcggt atctcaaact attgc                45

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgctctagat tacaaagctt cacgaatttt gtttgc                          36

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ccggaattcg ccgccaccat gcatgaaatc aaaaaagttt tggta                45

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tgctctagat tagaatggtt taccacgatg aatgat                          36

<210> SEQ ID NO 9
<211> LENGTH: 49
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 9
ccggaattcg ccgccaccat ggatattaaa tatacatgga atgttccga                49

<210> SEQ ID NO 10
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tgctctagat taatcgcgga ttttagcatg agtagc                              36

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gtgggccgct ctaggcacca a                                              21

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctctttgatg tcacgcacga tttc                                           24

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ttcaagctcc acttcaagct ctacagcgga ag                                  32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacagaaggc tatccatctc ctcagaaagt cc                                  32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

-continued tgcatcttgg ctttgcagct cttcctcatg gc                          32

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggacctgtg ggttgttgac ctcaaacttg gc                          32

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagctagttg tcatcctgct cttc                                   24

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgatgtgga cttggactca ttcatgg                                27

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtctgggcc actgccatgg agattc                                 26

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccattgccca ctctgtactc atcacac                                27

<210> SEQ ID NO 21
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

-continued ccggaattcg ccgccaccat ggaaactaac gcctgcagta tcaatgga       48

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tgctctagat tagagaatga caacatatgg atattc       36

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccggaattcg ccgccaccat ggatcaagtc gatgtcaaag attgtgcc       48

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tgctctagat taatcgcgga ttttagcatg agtagcaat       39

<210> SEQ ID NO 25
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccggaattcg ccgccaccat gattgttggt ggtgaaaaag cattagctg       49

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgctctagat tactgtgaac gttttgattc aatccaatcg ata       43

<210> SEQ ID NO 27
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ccggaattcg ccgccaccat ggaaacaagc gcttgccgta tcaattcg       48

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgctctagat tagaggttgt ttccggcttg gaaatatccg                          40

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccggaattcg ccgccaccat ggatcaaagt cgatgttaaa gattgtgcc                49

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tgctctagat taatcacgga ttttaccatg ggtagcaat                           39

<210> SEQ ID NO 31
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccggaattcg ccgccaccat gattgttggt ggtgtgaaag cacaagcc                 48

<210> SEQ ID NO 32
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tgctctagat tactgtgaac gttttgattc aatccaatcg ac                       42

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgggccgct ctaggcacca a                                              21

```
<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctctttgatg tcacgcacga tttc                                              24

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ttcaagctcc acttcaagct ctacagcgga ag                                     32

<210> SEQ ID NO 36
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacagaaggc tatccatctc ctcagaaagt cc                                     32

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgcatcttgg ctttgcagct cttcctcatg gc                                     32

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tggacctgtg ggttgttgac ctcaaacttg gc                                     32

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cagctagttg tcatcctgct cttc                                              24
```

```
<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtgatgtgga cttggactca ttcatgg                                       27

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtctgggcc actgccatgg agattc                                        26

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccattgccca ctctgtactc atcacac                                       27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
atgcaggact ttaagggtta cttgggt                                       27

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atttcggaga gaggtacaaa cgagg                                         25

<210> SEQ ID NO 45
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccggaattcg ccgccaccat gtcagcttat ttggcttacc gt                      42

<210> SEQ ID NO 46
```

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
tgctctagat tggaagcaca atcgactaat tct     33

<210> SEQ ID NO 47
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
ccggaattcg ccgccaccat gtatcgatac gttgcacgag aa     42

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
tgctctagat tgccaataat gacggcaat     29

<210> SEQ ID NO 49
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ccggaattcg ccgccaccat gcatgaaatc aaaaaaagtt ttggta     46

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
tgctctagat taacggcttc aattggaatt ct     32

<210> SEQ ID NO 51
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
ccggaattcg ccgccaccat gttagaagtt gatgttcccg gt     42

<210> SEQ ID NO 52
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
tgctctagat taacattttc agattttggt                                        30

<210> SEQ ID NO 53
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccggaattcg ccgccaccat gggtgatgat ggtgtttggc ct                          42

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tgctctagat taatcgcgga ttttagcatg agtagc                                 36

<210> SEQ ID NO 55
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ccggaattca tggaaactaa cgcctgcagt                                        30

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgctctagat tagagaatga caacatatgg atattc                                 36

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tgctctagat tggaagcaca atcgactaat tc                                     32

<210> SEQ ID NO 58
<211> LENGTH: 41
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 58
ccggaattcg ccgccaccat gtatcgatac gttgcacgag a                           41

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
tgctctagat tgccaataat gacggcaa                                          28

<210> SEQ ID NO 60
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ccggaattcg ccgccaccat gcatgaaatc aaaaaaagtt ttggt                       45

<210> SEQ ID NO 61
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
tgctctagat taacggcttc aattggaatt                                        30

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccggaattcg ccgccaccat gcgtggtatt                                        30

<210> SEQ ID NO 63
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gaatacatcc aacattgctc tagattattc tcgtgcaacg tatcgatagt a                51

<210> SEQ ID NO 64
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 64
ccggaattcg ccgccaccat gcatgaaatc                                    30

<210> SEQ ID NO 65
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aaaaaagttt tggtatgctc tagattagaa tggtttacca cgatgaatga t           51

<210> SEQ ID NO 66
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccggaattcg ccgccaccat ggatattaaa                                    30

<210> SEQ ID NO 67
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tatacatgga atgttccgat gctctagatt aatcgcggat tttagcatga gtagc       55

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtgggccgct ctaggcacca actctttgat gtcacgcacg atttc                  45

<210> SEQ ID NO 69
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ttcaagctcc acttcaagct ctacagcgga aggacagaag gctatccatc tcctcagaaa  60
gtcc                                                               64

<210> SEQ ID NO 70
<211> LENGTH: 64
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 70
tgcatcttgg ctttgcagct cttcctcatg gctggacctg tgggttgttg acctcaaact      60
tggc                                                                  64

<210> SEQ ID NO 71
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cagctagttg tcatcctgct cttcgtgatg tggacttgga ctcattcatg g               51

<210> SEQ ID NO 72
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tgtctgggcc actgccatgg agattcccat tgcccactct gtactcatca cac             53

<210> SEQ ID NO 73
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ccggaattcg ccgccaccat ggaaactaac gcctgcagta tcaatggatg ctctagatta      60
gagaatgaca acatatggat attc                                            84

<210> SEQ ID NO 74
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ccggaattcg ccgccaccat ggatcaagtc gatgtcaaag attgtgcctg ctctagatta      60
atcgcggatt ttagcatgag tagcaat                                         87

<210> SEQ ID NO 75
<211> LENGTH: 92
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ccggaattcg ccgccaccat gattgttggt ggtgaaaaag cattagctgt gctctagatt      60

```
actgtgaacg ttttgattca atccaatcga ta                                    92

<210> SEQ ID NO 76
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
ccggaattcg ccgccaccat ggaaacaagc gcttgccgta tcaattcgtg ctctagatta      60
gaggttgttt ccggcttgga aatatccg                                         88

<210> SEQ ID NO 77
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccggaattcg ccgccaccat ggatcaaagt cgatgttaaa gattgtgcct gctctagatt      60
aatcacggat tttaccatgg gtagcaat                                         88

<210> SEQ ID NO 78
<211> LENGTH: 90
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ccggaattcg ccgccaccat gattgttggt ggtgtgaaag cacaagcctg ctctagatta      60
ctgtgaacgt tttgattcaa tccaatcgac                                       90

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtgggccgct ctaggcacca actctttgat gtcacgcacg atttc                      45

<210> SEQ ID NO 80
<211> LENGTH: 64
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
ttcaagctcc acttcaagct ctacagcgga aggacagaag gctatccatc tcctcagaaa      60
gtcc                                                                   64

<210> SEQ ID NO 81
<211> LENGTH: 64
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tgcatcttgg ctttgcagct cttcctcatg gctggacctg tgggttgttg acctcaaact      60
tggc                                                                  64

<210> SEQ ID NO 82
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cagctagttg tcatcctgct cttcgtgatg tggacttgga ctcattcatg g               51

<210> SEQ ID NO 83
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
tgtctgggcc actgccatgg agattcccat tgcccactct gtactcatca cac             53

<210> SEQ ID NO 84
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
atgcaggact ttaagggtta cttgggtatt tcggagagag gtacaaacga gg              52
```

VACCINE FOR HOUSE DUST MITE ALLERGEN USING NAKED DNA

CROSS REFERENCE TO RELATED APPLICATION

The present application claims the benefit of U.S. Provisional Patent Application Ser. No. 60/121,547 filed Feb. 25, 1999, which is incorporated by reference in its entirety herein.

FIELD OF THE INVENTION

The present invention relates to a method of vaccination using naked DNA encoding T-cell epitopes, such as those of the house dust mite *Dermatophagoides pteronyssinus* (Der p) and *Dermatophagoides farinae* (Der f), which results in the suppression of IgE production. The present invention also relates to novel combinations of mixed plasmid DNA useful in IgE suppression.

BACKGROUND OF THE INVENTION

Genetic vaccination with naked plasmid DNA provides a long standing cellular and humoral immune response and promotes a shift in the pattern of cytokines produced by the T-cells. Peptides derived from T-cell epitopes can downregulate cytokine production and prevent specific antibody formation and administration of a single dominant epitope may tolerize the response to all the T-cell determinants within that protein.

About 15% of the world population exhibit a hypersensitivity response to common aeroallergens resulting in asthma, eczema, and rhinitis. The most frequently implicated allergens are derived from the house dust mite (HDM) including *Dermatophagoides pteronyssinus* (Der p) and *Dermatophagoides farinae* (Der f). From the serological analysis of IgE antibodies from HDM-allergic individuals, a major component (>90%) had a humoral response that was reactive with the group 1 and group 2 allergen. Therefore, using truncated recombinant proteins and overlapping peptides based on the nucleotide sequences, it is possible to generate T-cell epitope maps for human responses to HDM-derived allergens and to allow the development of immunotherapy. However, vaccines using peptides has a substantial limitation that in the peptides are poor immunogens. Recently, studies have shown it has revealed that genetic vaccinations with naked DNA provide long-lasting cellular and humoral immune responses. Long-term persistence of plasmid DNA and foreign gene expression in muscle suggested that muscle is an attractive target tissue for gene vaccination. Many studies have revealed that gene immunization with plasmid DNA encoding whole allergens or protein antigens induced strong T helper type (Th1) immune responses in mice and rats.

DESCRIPTION OF THE PREFERRED EMBODIMENTS

The present invention provides a method of vaccination using naked DNA encoding T-cell epitopes, such as those of the house dust mite *Dermatophagoides pteronyssinus* (Der p) and *Dermatophagoides farinae* (Der f), which results in the suppression of IgE production. The present invention also provides novel combinations of mixed plasmid DNA useful in IgE suppression.

The invention also includes a composition for reducing IgE production, comprising: a pharmacologically acceptable medium and a substantially pure, immunogenic plasmid DNA encoding a T-cell epitope. The present invention provides a method of reducing IgE production, comprising administering a composition comprising a pharmacologically acceptable medium and a substantially pure, immunogenic plasmid DNA encoding a T-cell epitope. The present invention also provides a vaccine for reducing the severity of an allergic disease in a mammal, comprising a pharmaceutically acceptable carrier and at least one plasmid DNA that encodes a T-cell epitope from a house dust mite antigen wherein the dust mite is selected from the group consisting of the house dust mite *Dermatophagoides pteronyssinus* (Der p), *Dermatophagoides farinae* (Der f) and mixtures thereof. The present invention further provides a composition for reducing IgE production, comprising: a pharmacologically acceptable medium and a substantially pure, immunogenic plasmid DNA encoding a major HDM allergen selected from the group consisting of Der p 1, Der p 2, Der p 3, Der f 1, Der f 2, Der f3 and mixtures thereof.

BRIEF DESCRIPTION OF THE DRAWINGS

The various features and advantages of the invention will be apparent from the attached drawings, in which like reference characters designate the same or similar parts throughout the figures, and in which:

FIG. 1B is a graph showing the Der p specific anti-IgE serum levels in mice versus number of weeks after immunization. FIG. 1C is a graph showing the Der p specific anti-IgG2a serum levels in mice versus number of weeks after immunization. FIG. 1D is a graph showing the Der p specific anti-IgG serum levels in mice versus number of weeks after immunization. FIG. 1E is a graph showing the Der p specific anti-IgG1 serum levels in mice versus number of weeks after immunization. FIG. 1F is a graph showing the IFN-γ serum levels in mice versus number of weeks after immunization. FIG. 1G is a graph showing the IL-4 serum levels in mice versus number of weeks after immunization.

Figure 1A:
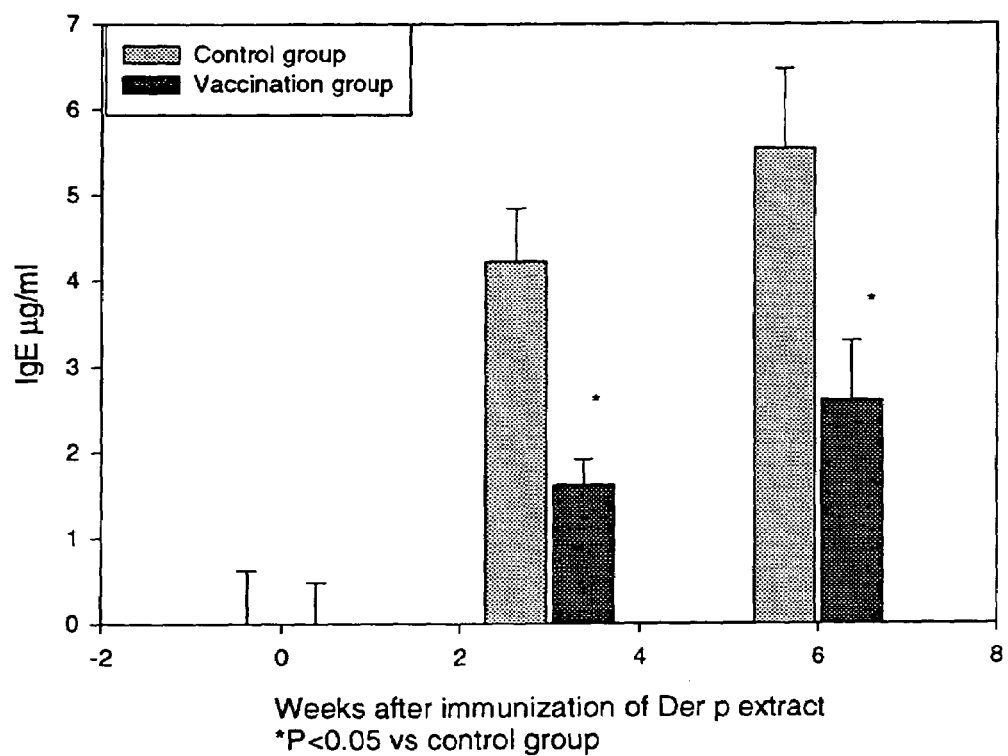
FIGS. 1A-G are graphs showing the serum levels in mice versus number of weeks after immunization.

The present invention will be further described in connection with the following Examples, which are set forth for purposes of illustration only. Parts and percentages appearing in such Examples are by weight unless otherwise stipulated.

EXAMPLES

Example 1

Human Epitope Vaccination

Introduction

To determine whether the vaccination with naked plasmid DNA encoding only a T-cells epitope peptide is able to suppress the allergic reaction in vivo, the mixed naked DNA plasmids encoding the five classes of human T-cell epitopes on Der p 1 and Der p 2 were used for genetic vaccination of BALB/c mice. The control mice were injected with the pcDNA 3.1 blank vector. There was a reduction in the total and Der p-specific immunoglobulin E (IgE) synthesis in the vaccinated mice compared with the control mice. In the Der p specific-IgG2a antibody response, the vaccinated mice showed more prominent responses than the control mice. Also analysis of the cytokines serum levels after immunization of Der p extract revealed that in the vaccinated mice there was an elevation in the level of interferon-γ, a Th1 cytokine associated with suppression of IgE production. The histologic studies showed that there was much less infiltration of inflammatory cells observed in lung tissue of the vaccinated mice than that of the control mice.

To evaluate whether the vaccination with naked plasmid DNA coding only a T-cell epitope peptide suppresses allergic reactions as effectively as the vaccination with DNA encoding whole allergen, an immune response to gene immunization with plasmid DNA encoding major T-cell epitopes in Der p 1 and 2 to challenges with whole Der p extract in mice to mimic realistic clinical setting was investigated. It was demonstrated that genetic vaccination indeed induced strong Th1 immune responses which reduced the IgE antibody production and allergic responses against Der p. Therefore, it would be ideal to develop an alternate naked DNA vaccination method which could be even safer than injecting whole segments of the allergen encoding region of either Der p1 or Der p2.

Materials and Methods

Mice

20 BALB/c mice at the age of 6-8 weeks were purchased from Jackson Laboratory (Bar Harbor, Me.) and bred at the University of Tennessee (Memphis, Tenn.). This study was performed in accordance with the PHS Policy on Humane Care and Use of Laboratory Animals, the NIH Guide for the Care and Use of Laboratory Animal Welfare Act (7 U.S.C. et seq.); the animal use protocol was approved by the Institutional Animal Care and Use Committee (IACUC) of the University of Tennessee.

Plasmid Construction

Total mRNA was isolated from Der p and Der f HDM, respectively. By using murine leukemia virus reverse transcriptase and random hexanucleotide primer following the instructions of the Perkin Elmer Gene Amp RNA PCR kit (Perkin Elmer, Branchberg, N.J.), first-strand cDNA was generated from 1 μg of total RNA and subjected to RT-PCR. The cDNA was used in PCR with Taq polymerase and with primers specific for human T-cell epitopes of Der p 1 and 2. These primers, which cover the mature excreted region of each genes and include EcoRI and XbaI sites for cloning, summarized in Table 1. The amplified PCR products were subcloned into pcDNA3.1 eukaryotic expression vector (Invitrogen, San Diego, Calif.) and then sequenced.

DNA Preparation and Vaccination

Each plasmid construct was prepared using Maxi prep (Qiagen, Chatsworth, Calif.). Mice were vaccinated by injection with 300 μg of pcDNA3.1 blank vector in 100 μl of PBS (control mice) or with 300 mg of the mixed naked DNA encoding the human T-cell epitopes of Der P 1 and 2 in 100 μl of PBS (vaccination mice) three times at weekly intervals into muscle.

Immunization and Inhalation of Allergen to Mice

The Der p-induced sensitivity in a mouse model was performed as described, Der p was emulsified with an equal volume of complete Freund's adjuvant (CFA) for immunization. Three weeks after last vaccination, mice were sensitized by injecting subcutaneously at the base of the tail with 100 μg of Der p extract in CFA. The mice were also given an intraperitoneal dose of 300 ng of purified pertussis toxin at 24 and 72 hours after first immunization. Seven days later, the mice were boosted again with the same amount of antigen in incomplete Freund's adjuvant. Mice received intranasally by inhalation intranasal with 10 μg of Der p extract six times at weekly intervals from boost.

Determination of Total and Der p-Specific IgE

The bloods from the 7 mice in two groups were collected three times on week 0 (first immunization), 3, and 6. The total IgE level was determined by ELISA as follows. One hundred microliters of anti-mouse IgE capture mAb (clone R35-72; Pharmingen, San Diego, Calif.) were added in each well to plate and incubated overnight at 4° C. After washing, two hundred microliters of 10% fetal calf serum were incubated at room temperature for 30 min. The plates were washed five times with washing buffer and incubated with the diluted mouse serum overnight at 4° C., followed by the addition of one hundred microliters of HRP-conjugated anti-mouse IgE detection mAb (clone R35-1 18; Pharmingen, San Diego, Calif.) overnight at 4° C. The plates were washed five times before adding citric acid-phosphate buffer (pH 5.0) containing 0.15 mg/ml of O-phenylenediamine (Sigma, St. Louis, Mo.). The color was developed at room temperature, and the reaction was stopped by 2.5 M sulfuric acid. The color was measured at 492 nm (Bio-Rad, Richmond, Calif.). The purified mouse anti-IgE antibody (Pharmigen, San Diego, Calif.) was used for total IgE standard. In the measure of the Der p specific IgE, the plate were coated with 25 μg/ml of Der p in 0.1 M carbonate buffer (pH 9.6) and serum samples were diluted fivefold in 10% FCS. The other procedures were the same as the measurement of Der p-specific IgE. The levels of Der p-specific IgE were referenced to the standard serum pooled from six mice that were immunized with 100 μg of Der p twice and inhaled with 10 μg of antigen six times. The standard serum was calculated as 100 ELISA units/ml.

Determination of Der p Specific IgG, IgG1, and IgG2a

The Der P specific IgG, IgG1, and IgG2a were determined by ELISA as follows. Purified antigens (5 μg/ml) were coated onto the assay plate and incubated overnight at 4° C. The other procedures were the same as the measurement of Der p-specific IgE.

Cytokines Serum Levels in Balb/c Mice after Immunization with Der p

Blood samples from the 7 mice in two groups were collected two times on week 0 (first immunization), and 2 weeks. The levels of IFN-γ and IL-4 were measured using the antibody pairs purchased from PharMingen, according to the manufacturer's instructions.

Histological Examination of Lung Tissue

Mice were anesthetized with a mixture of ketalar (35 mg/ml), rompun (0.6%/ml) and atropine (0.1 mg/ml), of which 0.2 ml was injected intramuscularly. The vascular bed of the lungs was perfused with 0.01 M Phosphate-buffered saline (PBS) and then with 4% paraformaldehyde 0.1 M PBS buffers. Whole lungs were taken out and were stored in 4% paraformaldehyde for 24 h at 4° C. After fixation, these tissues were dehydrated and embedded in paraffin. Frozen sections are cut at 6 μm in thickness were stained by hematoxylin and eosin. After coding, the sections were evaluated by two observers using light microscopy. The amount of mononuclear cells per section was scored using the method described by Hessel et al. This scoring method discriminates between the presence of mononuclear cells around blood vessels (score 0-3), and around bronchioli (score 0-3), and the number of patchy cellular infiltrates (score 0-3). Histological scores were analyzed using non-parametric Mann-Whitney U test. At least five mice were examined.

Lymph Node Cell Proliferation

The proliferation assay was performed as described. Briefly, 10 days after immunization, lymph nodes were removed aseptically, and single-cell suspension was prepared. The cells ($2\times10^5$ cells per well) were cultured with the serial dilution of Der p (range, 0.01-10 μg/ml). Cultures were set up in 200 μl RPMI1640 supplemented with 10% fetal calf serum (Hyclone Laboratories, Logan, Utah), 1 mmol/L sodium pyruvate, 100 μg/ml penicillin, 100 μg/ml streptomycin, 2 mmol/L glutamine, $5\times10^{-5}$ mol/L 2-mercaptoethanol, 20 mmol/L HEPES (pH 7.4), and 50× nonessential amino acids. After 72 hours culture, 1 μCi of [$^3$H] thymidine (Du Pont, Wilmington, Del.) was added to each well. Eighteen hours later, cells were harvested, and measured by liquid scintillation counting. Values were expressed in counts per minute as follows: Counts per minute with antigen-Counts per minute without antigen. Each sample was run in triplicate. RPMI medium 1640, sodium pyruvate, penicillin, streptomycin, glutamine, HEPES, and 50× nonessential amino acids were purchased from Irvine Scientific (Santa Ana, Calif.), and 2-mercaptoethanol was purchased from Sigma Chemical Co. (St. Louis, Mo.).

Statistical Analysis

The immunoglobulin response data was analyzed by Student's paired t test for comparisons between control and experimental mice. Histological grades were analyzed using a non-parametric Mann-Whitney U test. Data was expressed as mean ±SD. A P value <0.05 was considered significant.

Results

Suppression of total and Der p-specific IgE antibody production by gene vaccination.

Figure 1B:
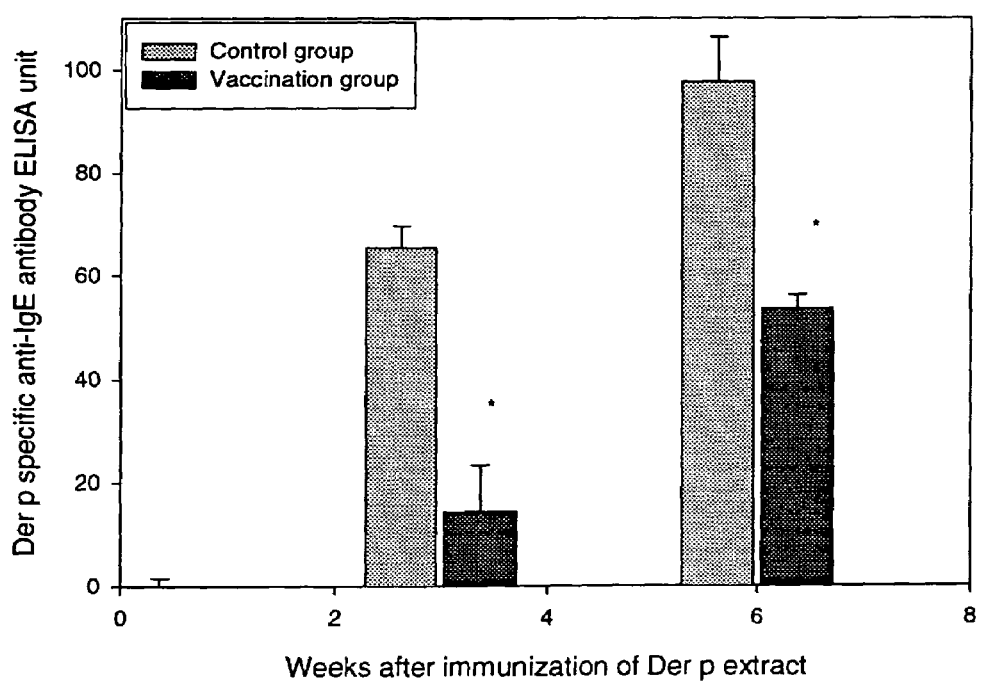
Figure 1C:
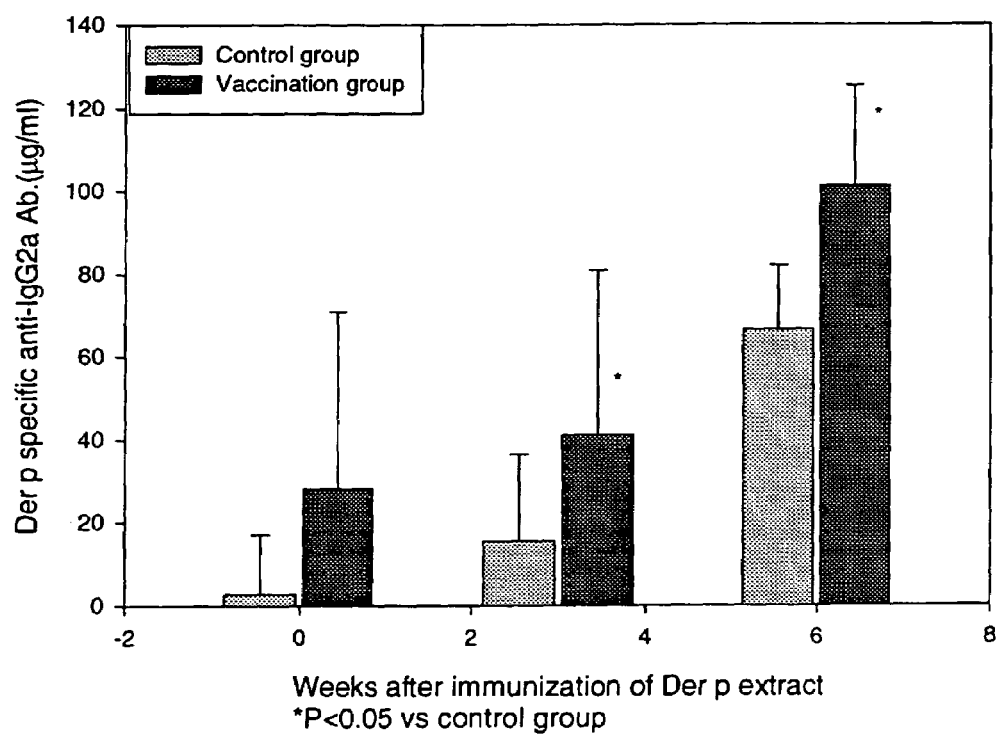
Figure 1D:
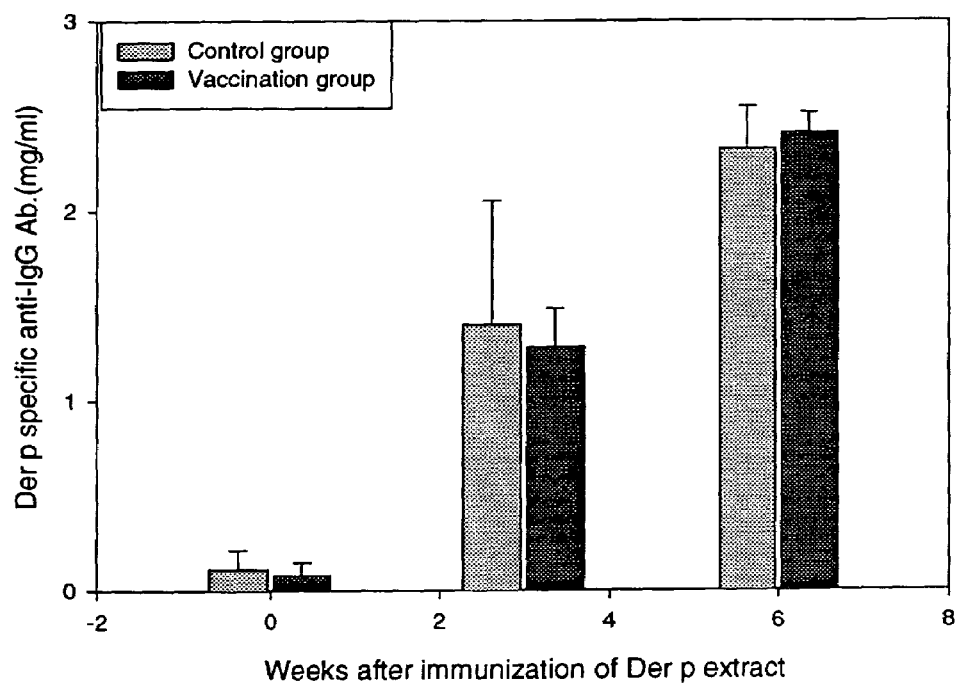
Figure 1E:
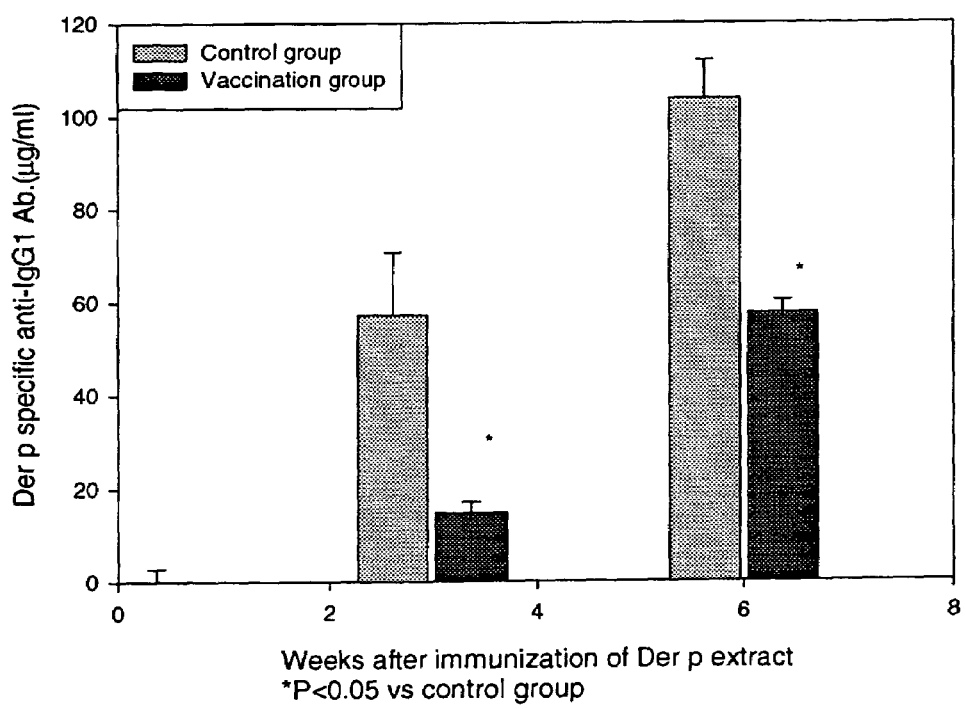

To determine the effect of vaccination with DNA encoding T-cell epitopes, we examined total and Der p specific IgE antibody levels by ELISA (FIGS. 1A and 1B). The gene vaccination with the human T cell epitopes of Der p 1 and 2 showed about 50% inhibition of Der p-specific IgE and more than 50% inhibition of total IgE as compared with the control mice at week 6. Thus, genetic vaccination could inhibit an in vivo allergen-specific IgE synthesis efficiently. To study the effects of DNA vaccination on B cell immunity, we measured Der p specific serum antibodies. The increase in production of Der p-specific IgG2a antibodies in the vaccination mice was greater than that in the control mice after 3 weeks although Der p specific IgG responses were similar between the two groups (FIGS. 1C and 1D). But in the Der p-specific IgG1 response, control mice showed more prominent production than vaccination mice (FIG. 1E).

Figure 1F:
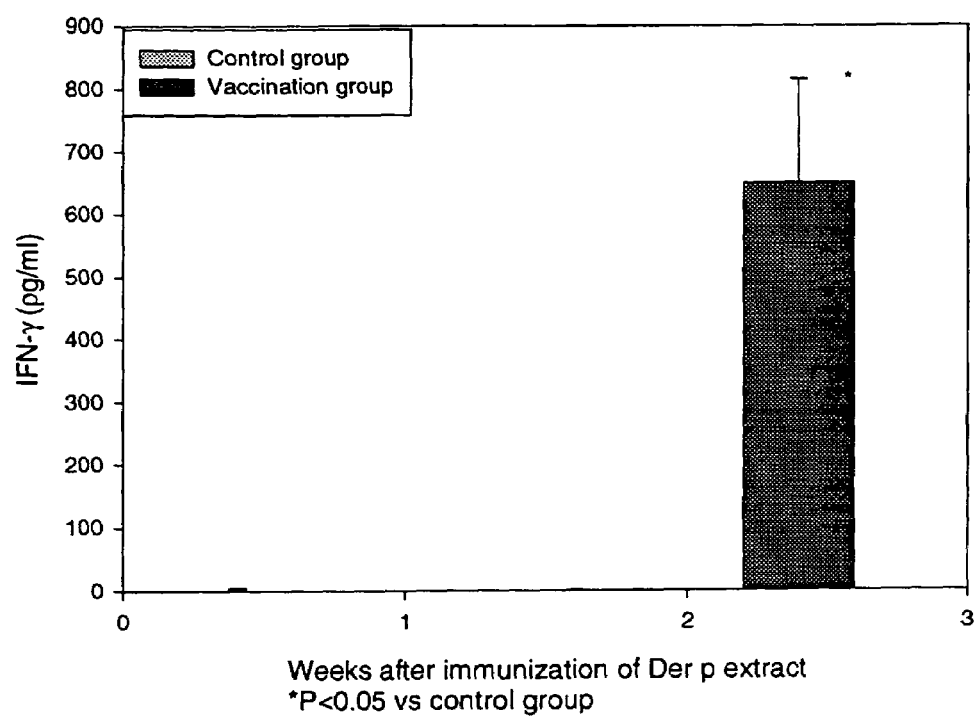
Figure 1G:
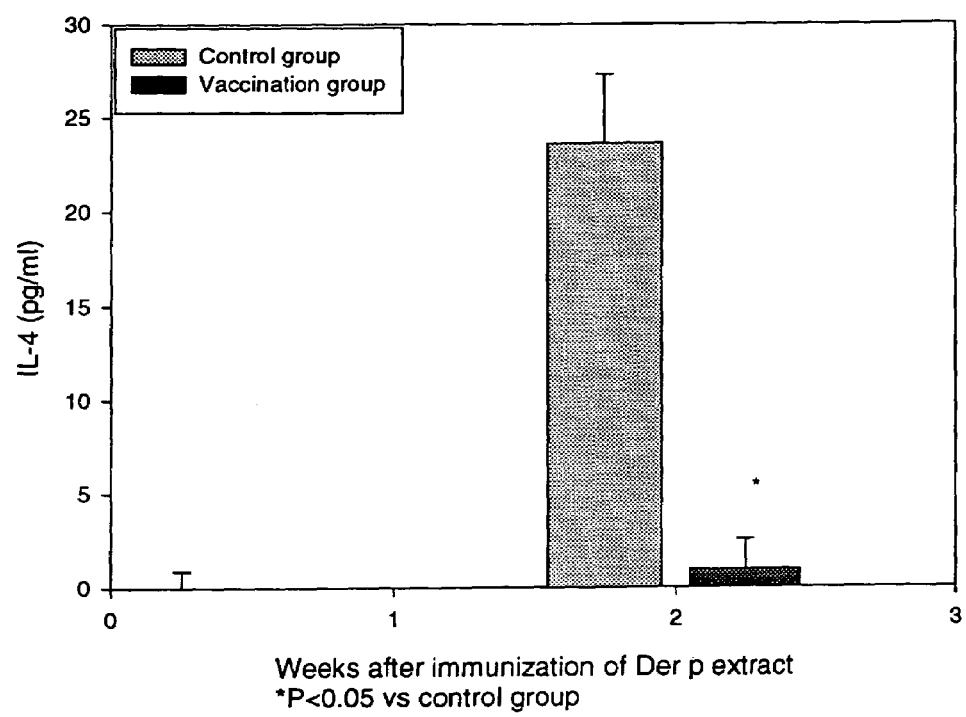

IFN-γ and IL-4 Serum Levels in Balb/c Mice after Immunization with Der p Extract To determine whether the Th1 or Th2 cytokines were produced in response to genetic vaccination with the human T-cell epitope genes, we measured IL-4 and IFN-γ serum levels. The IFN-γ serum level in vaccination mice (648.29±166.78 pg/ml) was observed to be higher than in control mice (undetectable) at 2 weeks after immunization of Der p extract (See FIG. 1F). In parallel, the IL-4 serum levels were detected contrary to the result of IFN-γ (control mice 23.63±3.66 pg/ml versus vaccination mice undetectable) (see FIG. 1G). Our results suggested that the genetic immunization with the plasmid DNA encoding T-cell epitopes might also induce a Th2 to Th1 cytokine shift.

Lymph Node Cells Proliferation

Figure 1H:
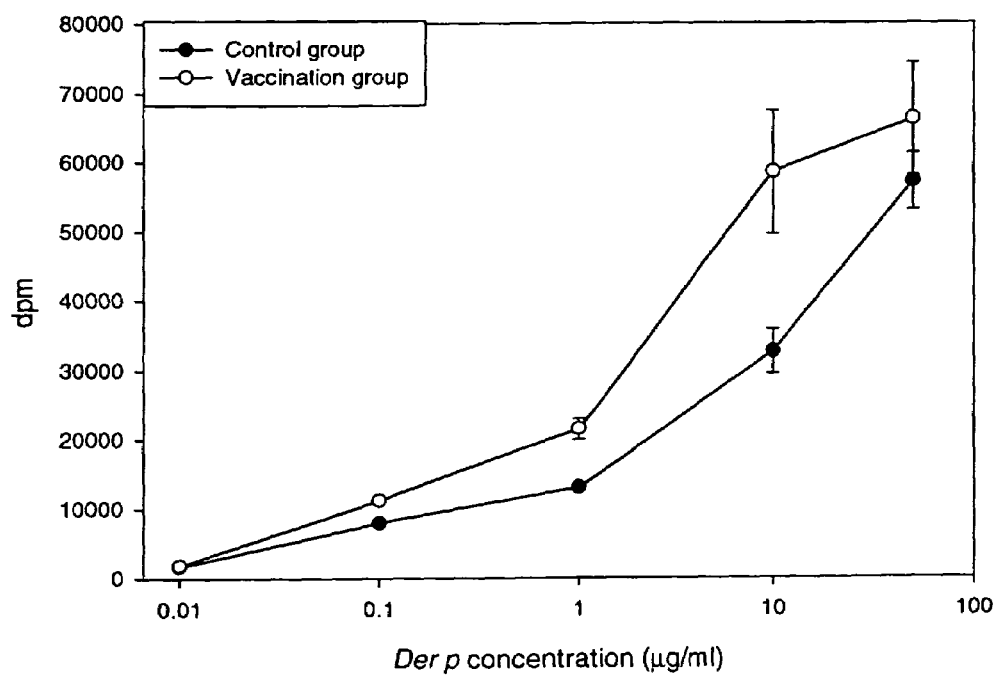
FIG. 1H is a graph showing cell proliferation versus concentration of Der p.

To determine whether the protective effect of gene vaccination was due to the deletion of T-cells or the induction of unresponsiveness, we examined lymph node cell proliferation in response to different concentrations of Der p. As seen in FIG. 1H, lymph node cells from the vaccinated mice showed a linear stimulation when concentration of Der p ranged from 0.01 μg/ml to 10 μg/ml, as did the lymph node cells from the control mice.

Histological Examination of Lung Tissue

To examine whether the genetic vaccination affected cellular response of lung or not, we stained the lung at the end of the experiment by histological method. The lung from the control mice showed an increase in the number of mononuclear cells infiltrates around bronchioli (mean number 1.5667±0.89 respectively, versus 0.5333±0.6756 in vaccination mice), and around blood vessels (mean number 0.8833±0.8847 respectively, versus 0.3833±0.6662 in vaccination mice) in comparison to the number of mononuclear cell infiltrates in the vaccination mice. Also control mice observed had significantly more patch cellular infiltrates than vaccination mice (mean number 1.3±1.0939 respectively, versus 0.35±0.6331 in vaccination mice).

Discussion

Diseases such as allergic asthma, rhinitis, and atopic dermatitis are all characterized by elevated levels of serum IgE. Total and specific IgE positively also showed a close relationship with clinical symptoms in atopic allergy. Analysis of antigen specificity of T-cell clones reactive with Der p 1 and Der p 2, with truncated recombinant proteins and synthetic peptides, has allowed several sites of T-cell recognition to be identified at different locations within Der p 1 and Der p 2. Several laboratories are now investigating the development of a new generation of immunotherapeutic strategies based on the modulation of T-cell function. Immunotherapy treatment has proven to be effective in treating some forms of allergy, but the antigen used was a poor immunogen and was needed at a higher concentration than the amount derived intracellularly from processed antigens. Recently gene immunization with naked DNA was shown to suppress induction of IgE synthesis. These data suggest that immunization with a plasmid DNA (Pdna) containing the gene for the minor HDM allergen Der p 5 may induce Th1 immune responses to the encoded antigens. The Der p 5 allergen reacts with about 40% of allergic sera but the Der p 1 and 2 allergens react with about 80% of allergic sera.[19,20] It was examined whether plasmid DNA encoding T-cell epitopes of human Der p 1 and Der p 2 would also be able to induce abrogation of allergic responses in mice when they are given the naked DNA vaccine. We have analyzed the effects of gene vaccination with a plasmid encoding T-cell epitopes of Der p 1 (residues 45-67, and 94-143) and Der p 2 (residues 11-40, 61-104, and 111-129).

Our results showed greater than 50% inhibition of total IgE and Der p-specific IgE at the end of the study (FIGS. 1A and 1B). Thus, this result suggested that gene vaccination with plasmid DNA encoding the T-cell epitopes could also suppress induction of IgE synthesis.

To determine whether the suppressive effect of gene vaccination was due to the deletion of T-cells or the induction of unresponsiveness, we examined lymph node cell proliferation in response to different concentrations of Der p. We found that lymph node cells taken from BALB/c mice were able to respond by proliferation depending on the Der p concentration, with a similar pattern to that of the cells taken from the control mice. T-cell deletion has mainly been observed after administration of high doses of antigen or peptide. Furthermore, numerous experimental systems have shown that presentation of antigen by nonprofessional antigen presenting cells (APCs) that lack co-stimulatory capacity results in anergy rather than priming.[23] But professional APCs, Langerhans cells or macrophages, may act as APCS for intramuscular DNA vaccination. Also our results demonstrate strong T-cell responses to varying concentrations of Der p. Thus, gene vaccination did not induce T-cell deletion or anergy. The T helper 2 (Th2) cells mainly produce IL-4, IL-5 and IL-10 which induce antibody production in B cells, including above all, the formation of IgE which plays a central role in allergic responses. IFN-γ is the Th1 cytokine responsible for the inhibition of IL-4-mediated IgE responses and promotes the formation of IgG2a. Protein immunization induces a Th2 response, as shown by IgG1 and IgE antibody formation and IL-4 and IL-5-secreting T-cells. In contrast, gene immunization with plasmid DNA induces a Th1 response with IgG2a antibody production and IFN-γ secreting T-cell. To study the immune mechanisms involved in suppression of IgE synthesis after DNA vaccination, we measured the IFN-γ and IL-4 serum levels in BALB/c mice after immunization of Der p extract. In the vaccinated mice there was an elevation in the Th1 cytokine IFN-γ associated with suppression of IgE synthesis. In parallel, there was a reduction in the Th2 cytokine IL-4. Lee et al reported that the Th1 response dominated over the Th2 response and downregulated preexisting IgE antibody formation after genetic immunization. Our results showed that the genetic immunization with the plasmid DNA encoding only T-cell epitopes might also induce a Th2 to Th1 cytokine shift.

To study the effects of DNA vaccination on B cell immunity, we measured Der p specific serum antibodies. At 6 weeks after immunization, total serum levels of IgG2a Der p specific antibody increased and the Der p specific IgG1 response was reduced in the vaccination mice compared with control mice although the Der p specific IgG responses were similar between the two groups. IgG2a is dependent on interferon-γ (IFN-γ) as an IgM-to-IgG2a switch factor and is believed to be typical for a Th1 response. In contrast, IgG1 depends on IL-4 secreted by Th2 cells.[28] The Der p specific IgG isotype data further indicated that genetic vaccination with DNA encoding the T-cell epitopes induces a Th2 to Th1 cytokine shift, since vaccination group had increased IgG2a levels compared with the levels of the control group. Our results suggested that genetic immunization might suppress IgE production by inducing a Th2 to Th1 cytokine shift.

Allergic asthma is characterized as a chronic inflammatory disease of the bronchi and it is well established that a variety of cells including mast cells, eosionphils and lymphocytes play a role in this process. After inhalation challenge, the inflammatory cells migrate from the peripheral blood to the site of inflammation in the bronchial mucosa and bronchoalveolar fluid shows dominant Th2-type cytokines. Our histological evaluation revealed that a significant number of patch mononuclear cell infiltrates were observed around the bronchioles and blood vessels in the vaccination mice compared with the control mice. T lymphocytes have been suggested to play a key role in orchestrating the interaction of the participating cells since they are able to release an array of cytokines which can attract, prime and activate other cell types. A successful outcome of immunotherapy has been associated with the development of suppressor T-cells, which can downregulate the allergic response. It has been suggested that the change in the function of T-cells might cause a reduction in the number of inflammatory cells infiltrating lung tissue. This data indicated that gene immunization affects not only humoral immune responses but also cellular responses.

The vaccination with mixed naked DNA encoding only T-cell epitopes might induce abrogation of allergic response in mice as effectively as DNA encoding whole segment allergen. Thus gene therapy using DNA encoding T-cell epitopes could be an ideal way of combating allergic disease in the future.

TABLE 1

Sequence of Primers for Human T-cell epitopes of Der p 1 and 2.

| | |
|---|---|
| Der p 1 epitope (residues 45-67) | 5'-CCG GAA TTC GCC GCC ACC ATG TCA GCT TAT TTG GCT TAC CGT-3' [SEQ. ID. NO:45] |
| | 5'-TGC TCT AGA TTG GAA GCA CAA TCG ACT AAT TCT-3' [SEQ. ID. NO:46] |
| Der p 1 epitope (residues 94-143) | 5'-CCG GAA TTC GCC GCC ACC ATG TAT CGA TAC GTT GCA CGA GAA-3' [SEQ. ID. NO:47] |
| | 5'-TGCTCT AGA TTG CCA ATA ATGACG GCA AT-3' [SEQ. ID. NO:48] |
| Der p 2 epitope (residues 11-40) | 5' CCG GAA TTC GCC GCC ACC ATG CAT GAA ATC AAA AAA AGT TTT GGT A-3' [SEQ. ID. NO:49] |
| | 5'-TGC TCT AGA TTA ACG GCT TCA ATT GGA ATT CT-3' [SEQ. ID. NO:50] |

TABLE 1-continued

Sequence of Primers for Human T-cell epitopes of Der p 1 and 2.

```
Der p 2 epitope      5'-CCG GAA TTC GCC GCC ACC ATG TTA GAA GTT
(residues 61-104)    GAT GTTCCCGGT-3' [SEQ. ID. NO:51]

5'-TGC TCT AGA TTA ACA TTT TCA GAT TTT GGT-3'
                     [SEQ. ID. NO:52]

Der p 2 epitope      5'-CCG GAA TTC GCC GCC ACC ATG GGT GAT GAT
(residues 111-129)   GGT GTT TGG CCT-3' [SEQ. ID. NO:53]

5'-TGC TCT AGA TTA ATC GCG GAT TTT AGC ATG
                     AGT AGC-3' [SEQ. ID. NO:54]
```

TABLE 2

Inflammatory cells in the lung tissue after immunization with Der p.

| Group | Around bronchioli | Around blood vessels | Patch cellular infiltrates |
|---|---|---|---|
| Control | 1.5667 ± 0.89 | 0.8833 ± 0.8847 | 1.3 ± 1.0939 |
| Vaccination | 0.5333 ± 0.6756* | 0.3833 ± 0.6662* | 0.35 ± 0.6331* |

*$P < 0.05$ compared with the control group

Example 2

The Effect of Vaccination with DNA Encoding Murine T-Cell Epitopes on Der p 1 and 2 Induced Immunoglobulin E Synthesis We would like to examine the effect of vaccination with DNA encoding only the murine T-cell epitopes on the IgE production. Our results suggested that genetic vaccination indeed induced the Th1 cytokine immune responses which in turn reduced the IgE antibody production and allergic responses against Der p. Therefore it would be ideal to develop an alternative naked DNA vaccination method which could be even safer than injecting whole segments of the encoding region of Der p 1 or Der p2.

Materials and Methods

Mice

20 BALB/c mice at the age of 6-8 weeks were purchased from Jackson Laboratory (Bar Harbor, Me.) and bred at the University of Tennessee (Memphis, Tenn.). This study was performed in accordance with the PHS Policy on Humane Care and Use of Laboratory Animals, the NIH Guide for the Care and Use of Laboratory Animal Welfare Act (7 U.S.C. et seq.); the animal use protocol was approved by the Institutional Animal Care and Use Committee (IACUC) of the University of Tennessee.

Plasmid Construction

Total mRNA was isolated from Der p and Der f HDM, respectively. By using murine leukemia virus reverse transcriptase and a random hexanucleotide primer following the instructions of the Perkin Elmer Gene Amp RNA PCR kit (Perkin Elmer, Branchberg, N.J.), first-strand cDNA was generated from 1 μg of total RNA and subjected to RT-PCR. The cDNA was used in PCR with Taq polymerase and primers specific for Der p 1 and 2 epitopes. These primers, which cover the mature excreted region of each genes and include EcoRI and XbaI sites for cloning are summarized in Table 3.

The amplified PCR products were subcloned into pcDNA3.1 eukaryotic expression vector (Invitrogen, San Diego, Calif.) and then sequenced.

DNA Preparation and Vaccination

Each plasmid construct was prepared using Maxi prep (Qiagen, Chatsworth, Calif.). Mice were vaccinated by injection with 300 Hg of pcDNA3.1 blank vector in 100 μl of PBS (control group) or with 300 mg of the mixed naked DNA encoding the murine T-cell epitopes of Der p 1 and 2 (vaccination group) three times at weekly intervals into muscle.

Immunization and Inhalation of Allergen to Mice

The Der p-induced sensitivity in a mouse model was performed as described. Der p was emulsified with an equal volume of complete Freund's adjuvant (CFA) for immunization. Three weeks after the last vaccination, mice were sensitized subcutaneously at the base of the tail with 100 μg of Der p extract in CFA. The mice were also given an intraperitoneal dose of 300 ng of purified pertussis toxin at 24 and 72 hours after first immunization. Seven days later, the mice were boosted again with the same amount of antigen in incomplete Freund's adjuvant. 10 μg of Der p extract was administered intranasally to the mice six times at weekly intervals from boost.

Determination of Der p Specific IgG1, IgG2a, and IgE

Blood from the 6 mice in two groups was collected six times on week 0 (first immunization), 3, and 6. The Der p specific IgG, IgG1, and IgG2a levels were determined by ELISA as follows. Fifty microliters of Der p (5 μg/ml in 0.1 M carbonate buffer, pH 9.6) were dispensed in each well of a polystyrene microtiter plate (Cost, Cambridge, Mass.) and incubated overnight at 4° C. The antigen-coated plates were washed three times in 0.05% PBS-Tween 20 buffer (washing buffer) and incubated with mice sera overnight at 4° C. The plates were washed five times with washing buffer and incubated with peroxidase conjugated anti-mouse IgG, IgG1, and IgG2a antibodies (Sigma, St. Louis, Mo.) overnight at 4° C. The plates were washed five times before adding citric acid-phosphate buffer (pH 5.0) containing 0.15 mg/ml of O-phenylenediamine (Sigma, St. Louis, Mo.). The color was developed at room temperature, and the reaction was stopped by 2.5 M sulfuric acid. The color was measured at 492 nm (Bio-Rad, Richmond, Calif.). In order to measure the Der p specific IgE, the plate were coated with 25 μg/ml HDM in 0.1 M carbonate buffer (pH 9.6) and serum samples were diluted fivefold in 10% FCS. The other procedures were the same as the measurement of Der p-specific IgG except HRP-conjugated anti-mouse IgE detection mAb (clone R35-118; Pharmingen, San Diego, Calif.). The level of Der p-specific IgE were referenced to the standard serum pooled from six mice that were immunized with 100 μg of HDM twice and inhaled 10 μg of antigen six times. The standard serum was calculated as 100 ELISA units/ml.

Histological Examination of Lung Tissue

Mice were anesthetized with a mixture of ketalar (35 mg/ml), rompun (0.6%/ml) and atropine (0.1 mg/ml), of which 0.2 ml was injected intramuscularly. The vascular bed of the lungs was perfused with 0.01 M Phosphate-buffered saline (PBS) and then with 4% paraformaldehyde 0.1 M PBS buffers. Whole lungs were taken out and were stored in 4% paraformaldehyde for 24 h at 4° C. After fixation, these tissues were dehydrated and embedded in paraffin. Frozen sections cut at 5 μm in thickness were stained by hematoxylin and eosin. After coding, the sections were evaluated by two observers using light microscopy. The amount of mononuclear cells per section was scored using the method described by Hessel et al. This scoring method discriminates between the presence of mononuclear cells around blood vessels (score 0-3), around bronchioli (score 0-3), and the number of patchy cellular infiltrates (score 0-3). Histological scores were analyzed using non-parametric Mann-Whitney U test. At least five mice were examined.

Immunohistochemical Staining for CD4+ and CD8+ T-Cells in Lung

The lung tissues from the experimental and control group mice were removed after the final intranasal inhalation. The tissues were fixed with periodat-lysine-paraformaldehyde solution for 24 h at 4° C. Frozen sections cut at 4 to 6 μm in thickness were rehydrated and rinsed in cold PBS. The endogenous pseudoperoxidase was blocked with absolute methanol containing 0.5% hydrogen peroxide for 20 min at room temperature. The sections were treated with 10% normal goat serum in PBS to reduce the nonspecific binding. Biotin conjugated rat anti-mouse CD8 or CD4 monoclonal antibody (Pharmingen, San Diego, Calif.), diluted to 1:200 in PBS containing 0.5% bovine serum albumin, was applied to the sections and incubated overnight at 4° C. After rinsing, the sections were incubated with avidin-biotin peroxidase complexes (Vectastain Elite ABC Kit, Vector Laboratories Inc., Burlingame, Calif.) for 30 min at room temperature and rinsed sufficiently with PBS. The reaction was developed with 0.02% 3,3'-diaminobenzidine in 0.05 M of Tris buffer (pH 7.6) with 0.005% hydrogen peroxide for 7 min. The sections were dehydrated, cleared in xylene, and mounted.

Measuring Cytokine mRNA Expression

Mice from two groups were sacrificed 10 days after immunization with Der p extract. The lymph nodes were removed from mice and stimulated with recombinant Der p (100 μg/ml) in vitro for 18 hrs. The cells were washed with PBS buffer and mRNAs prepared (Biotecx, Houston, Tex.). By using murine leukemia virus reverse transcriptase and random hexanucleotide primers following the instructions of the Perkin Elmer Gene Amp RNA PCR kit (Perkin Elmer, Branchberg, N.J.), first-strand cDNA was generated from 1 μg of total RNA and subjected to RT-PCR analysis. To determine the relative abundance of each cytokine mRNA expression, the amount of each cDNA for PCR was optimized by the intensity of the amplified DNA products of β-actin from each RNA. In the PCR reaction mixture, either β-actin as the control primer, IL-2, IFN-γ (Clonetech, PaloAlto, Calif.), IL-4, or IL-5 at the final concentration of 0.2 μM were added. The PCR condition was as follows: 200 μM of dNTP, 10 μCi [32P] dCTP, 50 μM Tris. HCl (pH 9.0), 50 μM NaCl, 2 μM MgCl2, 0.5 mM DTT, and two units of Taq polymerase (Perkin Elmer, Branchberg, N.J.) at a final volume of 20 μl. A negative control reaction was run with each sample to verify that no PCR bands appeared in the absence of template. The optimal amplification conditions were as follows: 45 s at 94° C. for denaturation, 45 s at 67° C. for annealing, and 1 min at 72° C. for elongation and the PCR cycles were 30. The amplified DNAs of β-actin, IFN-γ, IL-2, IL-4, and IL-5 had sizes of 540, 365, 413, 354, and 349 base pairs, respectively. The gel was dried on Whatman 3M paper and exposed to Kodak XAR film. In each electrophoresis run, intra- and inter-gel staining homogeneity was confirmed by staining intensity of molecular weight markers at both ends of the gels. In general, amplification kinetics were monitored for each PCR run by examining aliquots of the products on the gel. Amounts of the PCR products were compared during the cycles where the amplification did not reach saturation.

Statistical Analysis

The immunoglobulin response data was analyzed by Student's paired t test for comparisons between control and experimental group. Histological grades were analyzed using a non-parametric Mann-Whiney U test. Data was expressed as mean ±SD. A P value <0.05 was considered significant.

Results

Der p-Specific IgE, IgG1, IgG2a, and IgG Antibody Responses by Gene Vaccination.

Figure 2A:
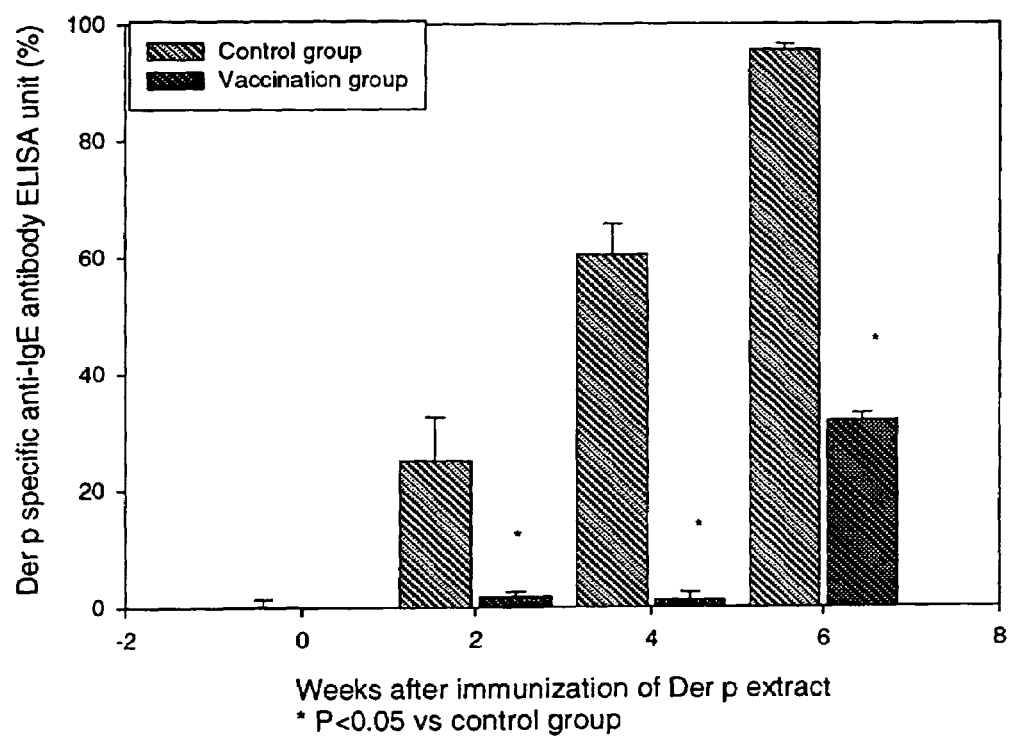
FIG. 2A is a graph showing Der p specific IgE serum levels in mice versus number of weeks after immunization.
Figure 2B:
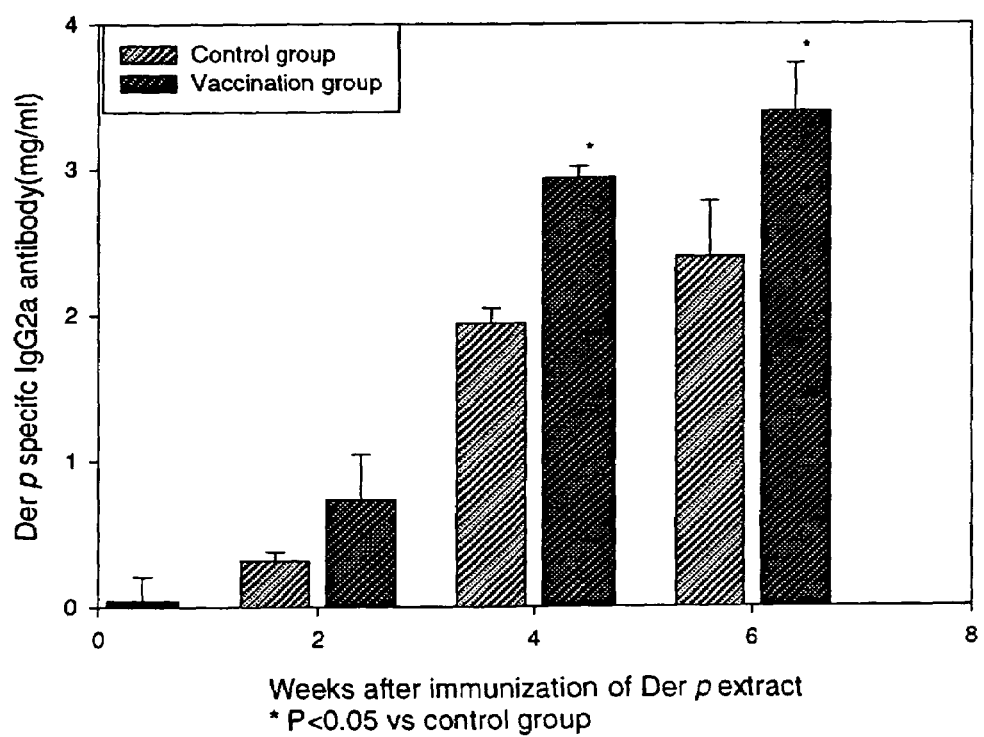
FIG. 2B is a graph showing the Der p specific IgG2a serum levels in mice versus number of weeks after immunization.
Figure 2C:
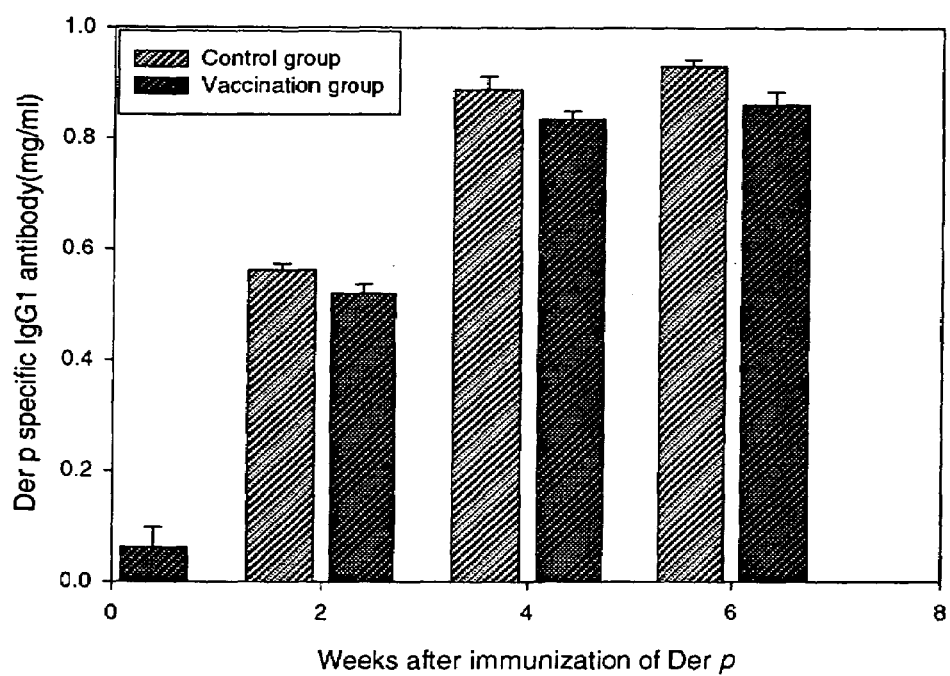
FIG. 2C is a graph showing the Der p specific IgG1 serum levels in mice versus number of weeks after immunization.
Figure 2D:
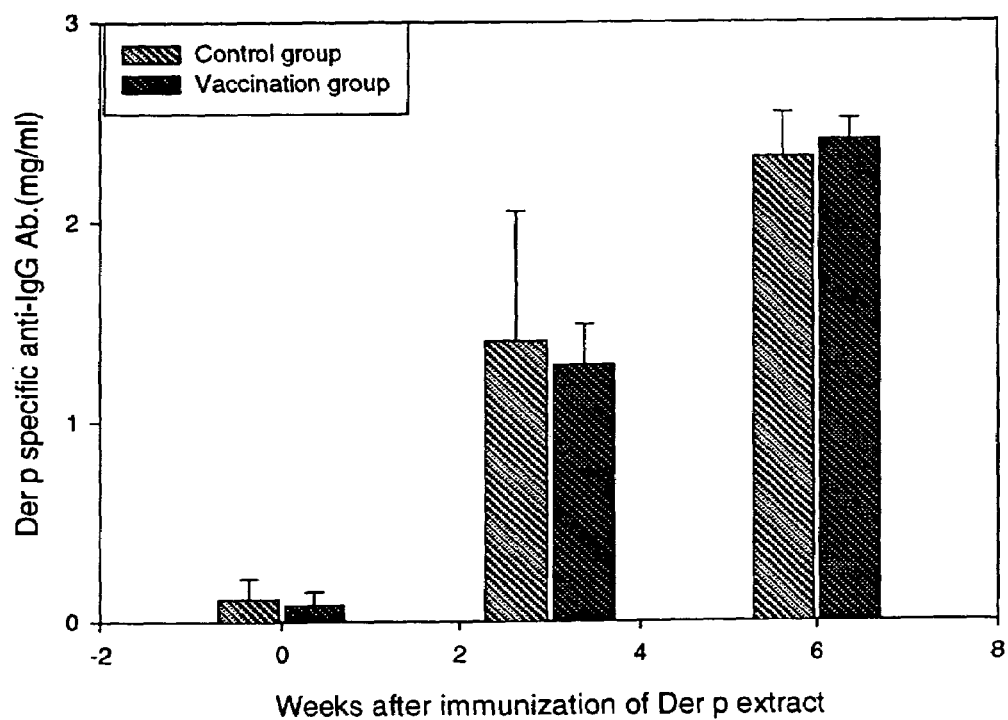
FIG. 2D is a graph showing the Der p specific anti-IgG serum levels in mice versus number of weeks after immunization.
Figure 2E:
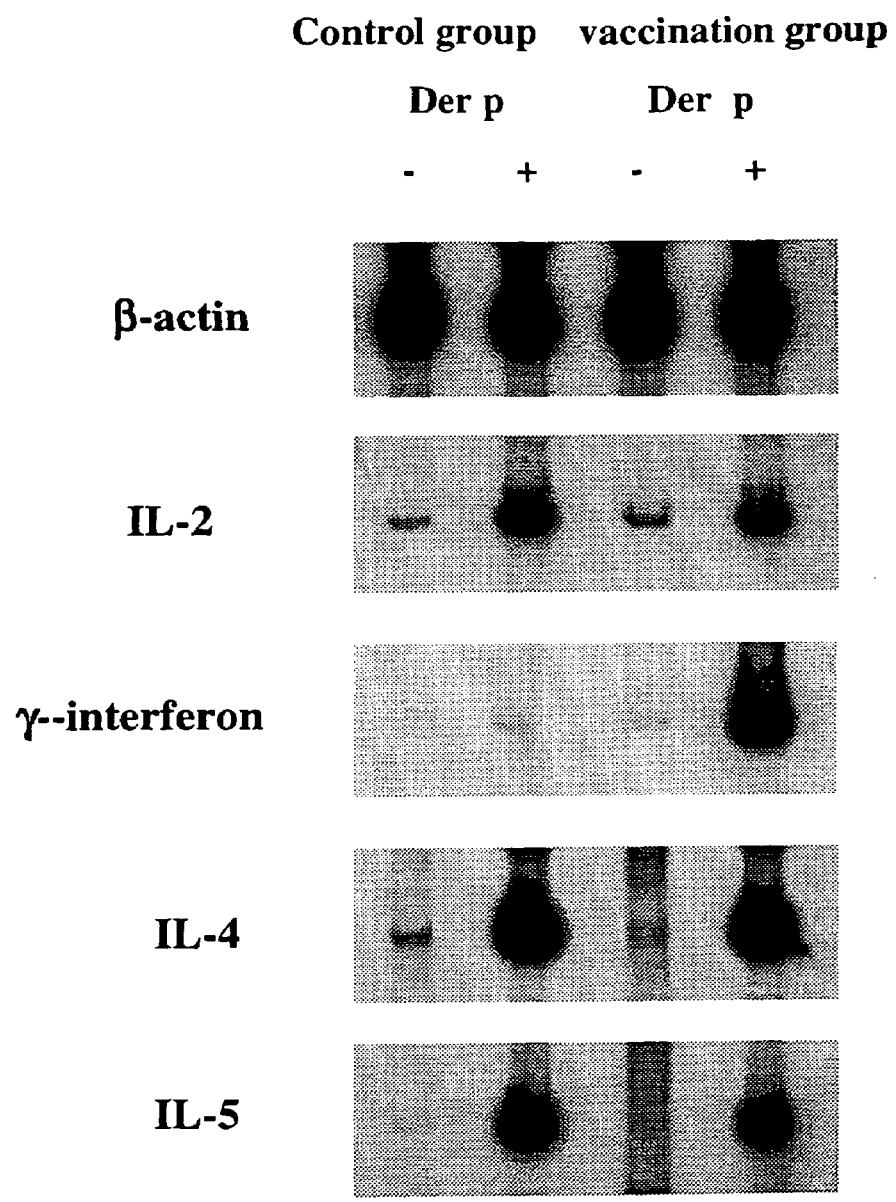
FIG. 2E is an autoradiograph showing the levels of mRNA expression in control and vaccinated mice.
Figure 2F:
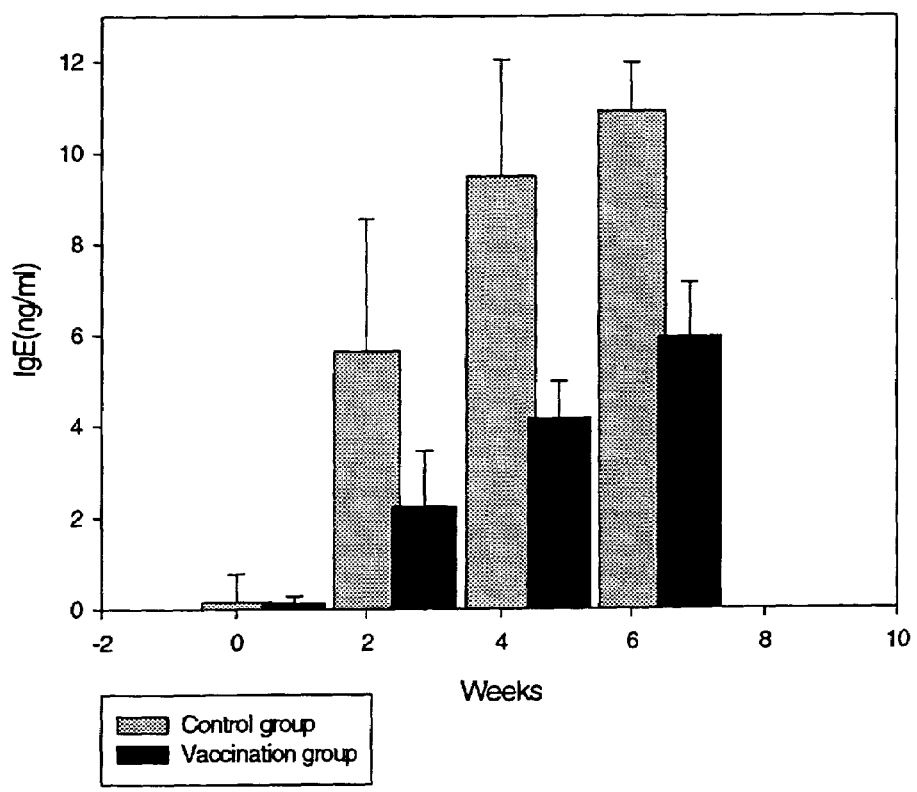
FIG. 2F is a graph showing the total IgE serum level in mice after intramuscular injection versus weeks after immunization.

To examine the immune response, we checked the levels of IgG, IgG1, G2a, and IgE antibody productions by ELISA (FIG. 2B C, D, F.). The gene vaccination with the murine T-cell epitope of Der p 1 and 2 showed about 60% inhibition of Der p-specific IgE as compared with the control group at week 6 (FIG. 2A). Thus, genetic vaccination could inhibit an in vivo allergen-specific IgE synthesis efficiently. The production of Der p-specific IgG2a antibodies in the vaccination group was greater than that in the control group after 6 weeks (FIG. 2B). However, in the Der p-specific IgG1, and IgG responses, the two groups did not show any difference (FIGS. 2C and 2D).

Cytokine Gene Expression by Antigen Stimulation In Vivo

Figure 3A:
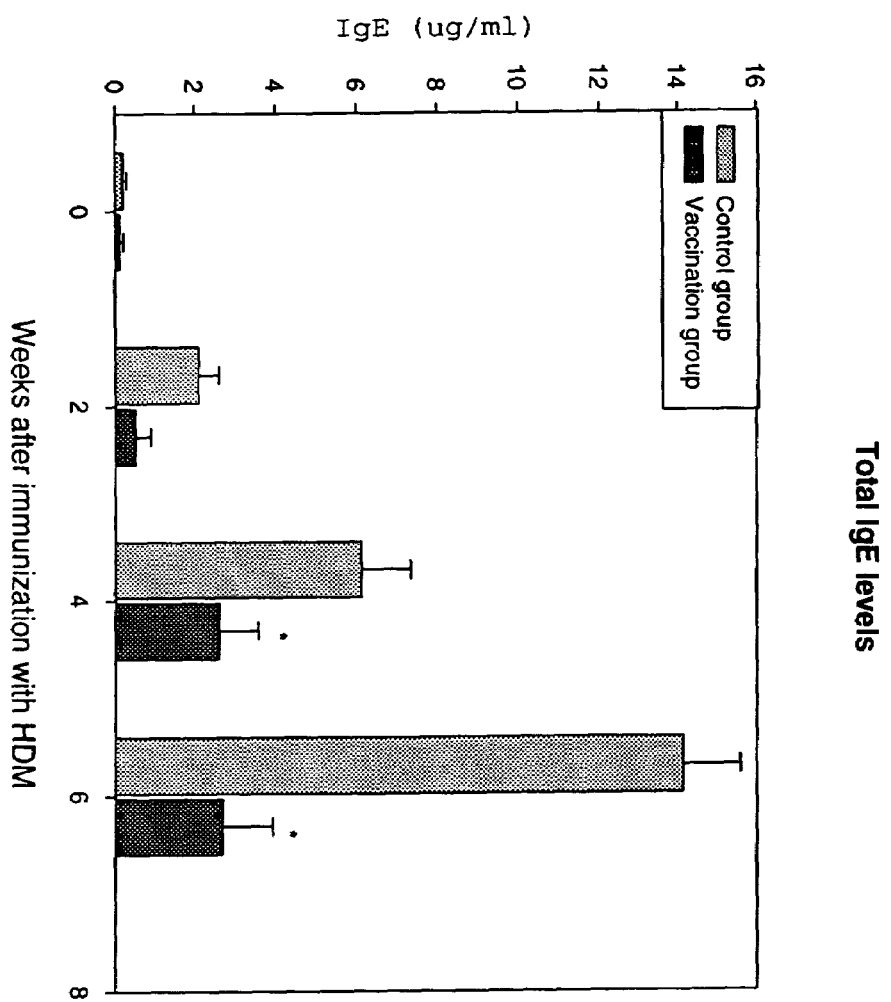
FIGS. 3A-C are graphs showing antibody levels in mice versus weeks after immunization where the antibody measure is (A) total IgE, (B) HDM-specific IgE, or (C) HDM-specific IgG.
Figure 3B:
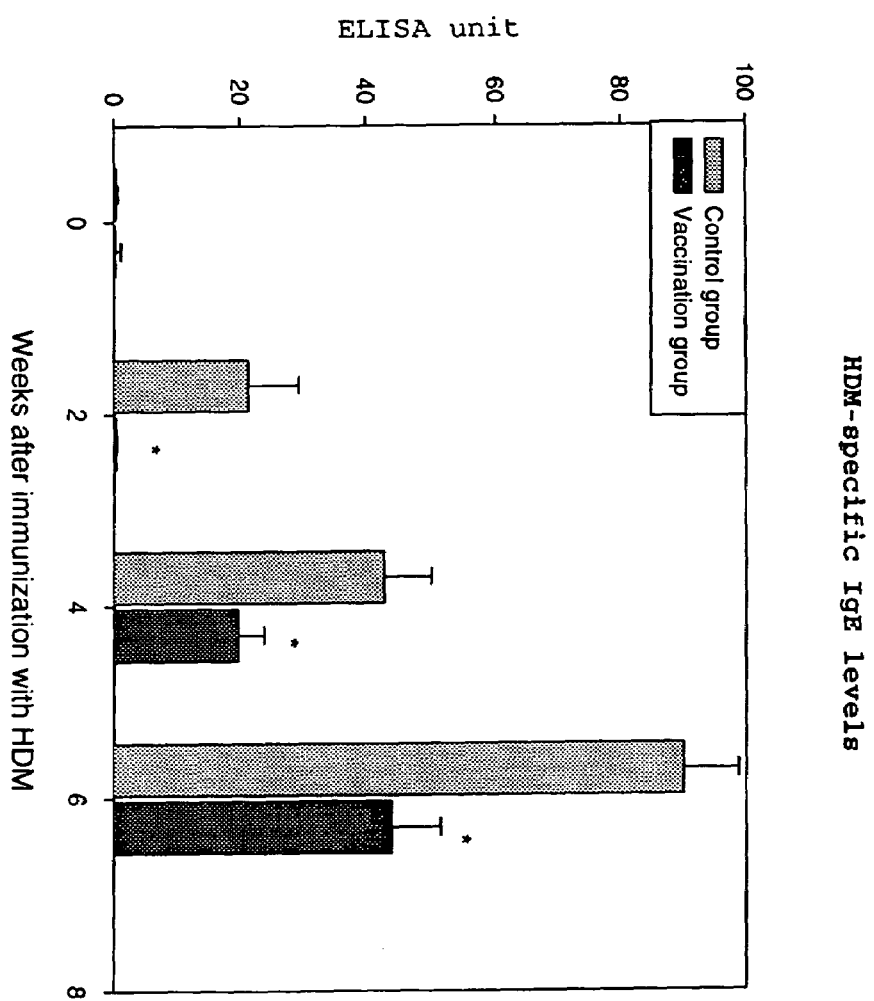

To determine whether the Th1 or Th2 cytokines are involved in the genetic vaccination, we performed a RT-PCR analysis on the total RNA samples extracted from lymph node cells ($1 \times 10^7$ cells per well) that were cultured in the presence of Der p (100 μg/ml) in vitro for 18 hrs. A higher mRNA expression of IFN-γ in the vaccination group was detected compared with the control group. The level of mRNA expression of IL-2, 4 and 5 in the vaccination group were similar to the level in comparing of the control group (FIG. 3). These data indicate that the vaccinations with Der p epitope DNA predominantly increased Th1 cytokine (IFN-γ) gene expression in the lymph node.

Histological and Immunohistochemical Examination of Lung Tissue

To examine whether the genetic vaccination affected cellular response of lung or not, we stained the lung at the end of the experiment by histological and in immunohistochemical methods. The lungs from the control group showed much more infiltration of inflammatory cells around bronchioli, blood vessels, and interstitium (table 5, FIG. 4). In the immunohistochemical stain for CD4+ and CD8+, T-cells showed that more CD8+ T-cells infiltrated in the submucosa and mucosa of the lung from the vaccination group (94.5±6.75/mm) as compared with the control group (49±4.966/mm). The stain for the CD4+ T-cells showed no difference between the two groups (vaccination group 98.5±13.44/mm versus control group 114±11.31/mm). The results suggest that the genetic vaccination also affects the cellular response. and the CD8+ T-cells of the vaccination were capable of protecting against a subsequent allergenic challenge.

Discussion

Diseases such as allergic asthma, rhinitis, and atopic dermatitis are all characterized by elevated levels of serum IgE. Total and specific IgE positivity also have showed a close relationship with clinical symptoms in atopic allergy. A variety of approaches targeting the suppression of IgE have been proposed using synthetic peptides as a T-cell vaccine. However, the synthetic peptides were poor immunogens and were needed at higher levels than the amount derived intracelluarly from processed antigens. Recently Hsu et al. showed that gene immunization of rats with plasmid encoding Der p 5 prevents induction of IgE synthesis. These data suggest that plasmid DNA (pDNA) immunization with a plasmid containing the gene for the minor HDM allergen Der p 5 may induce a Th1 immune responses to the encoded antigens. The Der p 5 allergen reacts with about 40% of allergic sera but the Der p 1 and 2 allergens react with about 80% of allergic sera.[3,5] We have analyzed the effects of gene vaccination with plasmid DNA encoding only the murine T-cell epitopes in allergic responses to whole Der p extract. Our results showed about 70% inhibition of Der p-specific IgE 6 weeks after immunization with Der p (FIG. 2A).

Animal models have established that Th2 responses are mediated by T helper cells that secret cytokines such as IL-4 and IL-5 that induce antibody production in B cells, including above all, the formation of IgE which plays a central role in allergic responses.[19,20] IFN-γ is the Th1 cytokine responsible for the inhibition of IL-4-mediated IgE responses and promotes the formation of IgG2a.[21] Previous reports showed that protein immunization induced a Th2 response, as shown by IgG1 and IgE antibody formation and IL-4 and IL-5-secreting T-cells. In contrast, gene immunization with plasmid DNA induced a Th1 response with IgG2a antibody production and IFN-γ secreting T-cells. Our data showed that the mRNA expression of IFN-γ in lymph nodes from plasmid DNA encoding the murine T-cell epitopes of Der p 1 and 2 increased more than the expression in the control group, and this increase may be associated with suppression of IgE synthesis. In parallel, in a Th2 response, there was no difference between the two groups. Our results suggested that the genetic immunization might induce a Th1 immune response to the encoded antigen or allergen. After genetic immunization, the Th1 response dominated over the Th2 response and suppressed preexisting IgE antibody formation.

Gamma interferon promotes the formation of IgG2a and inhibits IgE production[13] although the mechanism through which IFN-γ exerts its stimulatory effects on IgG2a production has not been established. Our data also showed that the production of IgG2a-anti-Der p antibody was higher in the vaccination group than the control group. Our results suggest that genetic immunization might suppress IgE production by inducing the Th1 response from T helper cells.

Figure 4:
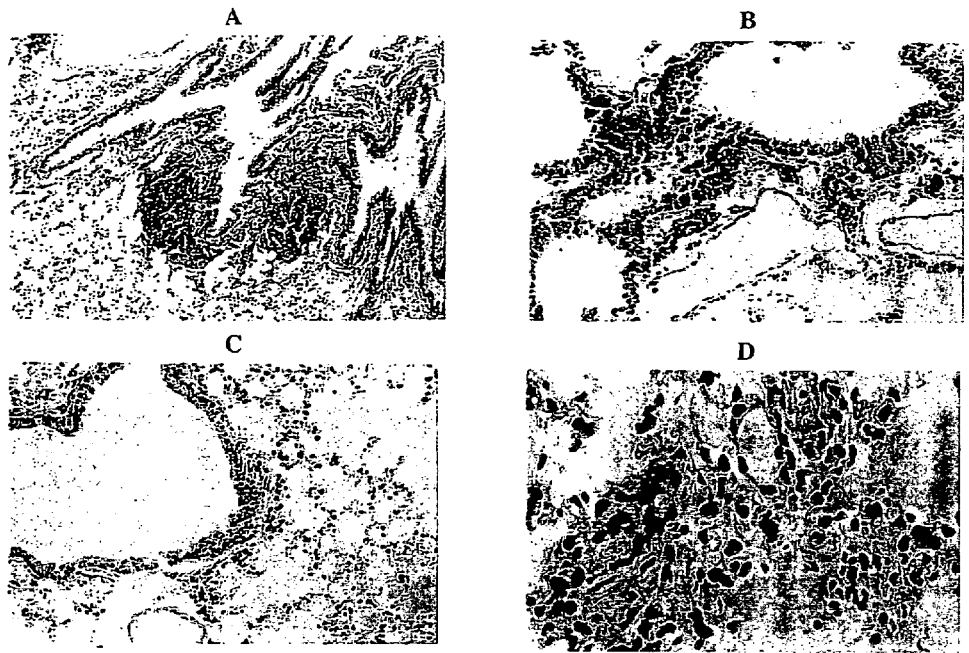
FIGS. 4A-C are photomicrographs of lung tissue from control or vaccinated mice where the samples are (A) lung from a control mouse (×100), (B) lung from control mouse (×200), (C) lung from vaccination mouse (×200), and (D) bronchial wall from control mouse (×600).

Allergic asthma is characterized as a chronic inflammatory disease of the bronchi and it is well established that a variety of cells including mast cells, eosinophils and lymphocytes play a role in this process. After an inhalation challenge, the inflammatory cells migrate from the peripheral blood to the site of inflammation in the bronchial mucosa and bronchoalveolar fluid and the cells predominantly express Th2-type cytokines. Our histological study showed that gene vaccination induced the reduction of infiltration of inflammatory cells in lung tissues (FIG. 4). It suggested that the change in the function of T-cells might cause a reduction of the inflammatory cells in lung tissue. These results suggested that genetic immunization affected not only humoral immune responses but also cellular responses.

T lymphocytes have been suggested to play a key role in orchestrating the interaction of the participating cells because they are able to release an array of cytokines which can attract, prime and activate other cell types. A successful outcome of immunotherapy has been associated with the development of suppressor T-cells, which can downregulate the allergic response. A recent report has also revealed that functionally distinct subsets of CD8+ T-cells may play an important regulatory role in IgE production. However, Manickan et al showed that the mechanism of genetic immunization was principally by CD4+ T-cells, but not by CD8−+− T-cells. Our immunohistochemical study showed that more CD8+ T-cells were detected in the lung of the vaccination group than that of the control group. Peptides derived from cytosolic proteins are generally presented to CD8+ T-cells by major histocompatibility complex (MHC) class I molecules which are expressed on virtually all somatic cells. The results suggested that such endogenous production of an allergenic protein might be a useful means to induce regulatory CD8+ T-cells capable of conferring protection against a subsequent allergenic challenge.

The vaccination with mixed naked DNA encoding only T-cell epitopes might induce an abrogation of allergic response in mice as effectively as DNA encoding whole segment allergen. Thus genetic vaccination using DNA encoding T-cell epitopes could be an ideal way of combating allergic disease in the future.

TABLE 3

Sequence of Primers for the murine Der p 1 and 2 epitopes

| | |
|---|---|
| Der p 1 epitope (residues 21-49) | 5'-CCG GAA TTC GCC GCC ACC ATG ACT GTC ACT CCC ATT CGT ATG C-3' [SEQ. ID. NO:1] |
| | 5'-TGC TCT AGA TTA AGC CAA ATA AGC TGA TTC AGT TGC-3' [SEQ. ID. NO:2] |
| Der p 1 epitope (residues 78-100) | 5'-CCG GAA TTC GCC GCC ACC ATG CGT GGT ATT GAA TAC ATC CAA CAT-3' [SEQ. ID. NO:3] |
| | 5'-TGC TCT AGA TTA TTC TCG TGC AAC GTA TCG ATA GTA-3' [SEQ. ID. NO:4] |
| Der p 1 epitope (residues 110-131) | 5'-CCG GAA TTC GCC GCC ACC ATG CGT TTC GGT ATC TCA AAC TAT TGC-3' [SEQ. ID. NO:5] |
| | 5'-TGC TCT AGA TTA CAA AGC TTC ACG AAT TTT GTT TGC-3' [SEQ. ID. NO:6] |

TABLE 3-continued

Sequence of Primers for the murine Der p 1 and 2 epitopes

Der p 2 epitope  5'-CCG GAA TTC GCC GCC ACC ATG CAT GAA ATC AAA AAA GTT
(residues 11-35) TTG GTA -3' [SEQ. ID. NO:7]

5'-TGC TCT AGA TTA GAA TGG TTT ACC ACG ATG AAT GAT-3'
[SEQ. ID. NO:8]

Der p 2 epitope   5'-CCG GAA TTC GCC GCC ACC ATG GAT ATT AAA TAT ACA TGG
(residues 87-129) AAT GTT CCG A-3' [SEQ. ID. NO:9]

5'-TGC TCT AGA TTA ATC GCG GAT TTT AGC ATG AGT AGC-3'
[SEQ. ID. NO:10]

TABLE 4

Oligonucleotides used for cytokine mRNA expression

| Molecules | Primer Sequence (5' to 3') | Product Size |
|---|---|---|
| β-actin | 5'-GTG GGC CGC TCT AGG CAC CAA-3' [SEQ. ID. NO:11] | 540 bp |
| | CTC TTT GAT GTC ACG CAC GAT TTC-3' [SEQ. ID. NO:12] | |
| IL-2 | 5'-TTCAAGCTCCACTTCAAGCTCTACAGCGG AAG-3 [SEQ. ID. NO:13] | 413 bp |
| | GACAGAAGGCTATCCATCTCCTCAGAAAG TCC-3' [SEQ. ID. NO:14] | |
| IFN-γ | 5'-TGCATCTTGGCTTTGCAGCTCTTCCTCAT GGC-3' [SEQ. ID. NO:15] | 365 bp |
| | TGGACCTGTGGGTTGTTGACCTCAAACTT GGC-3' [SEQ. ID. NO:16] | |
| IL-4 | 5'-CAG CTA GTT GTC ATC CTG CTC TTC-3' [SEQ. ID. NO:17] | 357 bp |
| | 5'-GTG ATG TGG ACT TGG ACT CAT TCA TGG-3' [SEQ. ID. NO:18] | |
| IL-5 | 5'-TGT CTG GGC CAC TGC CAT GGA GAT TC-3' [SEQ. ID. NO: 19] | 424 bp |
| | 5'-CCA TTG CCC ACT CTG TACT CA TCA CAC-3' [SEQ. ID. NO:20] | |

TABLE 5

Inflammatory cells in the lung tissue after immunization with Der p

| Group | Around Bronchioli | Around blood vessels | Patch Cellular Infiltration |
|---|---|---|---|
| Control | 1.5616 ± 0.7262 | 1.6438 ± 1.2733 | 1.6471 ± 0.4926 |
| Vaccination | 0.6835 ± 0.4947* | 0.3924 ± 0.5168* | 0.3333 ± 0.4815* |

*P < 0.05 compared with the control group

FIG. 2a. Effect of vaccination on the allergen induced immuoglobulin E production. Blood from the 6 mice in two groups was collected three times on week 0 (first immunization), 3 and 6. The gene vaccination with the murine T-cell epitopes on Der p 1 and 2 showed about 70% inhibition of Der p-specific IgE as compared with the control mice at week 6. Data shown are mean ±S.D. (n=6 per group). *P<0.05 compared with the control mice.

FIG. 2. The IgG2a (B), IgG1 (C), and IgG (C) antibody responses of BALB/c mice after immunizing with Der p extract. The production of Der p-specific IgG2a antibodies in the vaccination mice increased more than that in the control mice after 3 weeks (FIG. 2A). But in the Der p-specific IgG1 and IgG responses, there was no difference between the two groups (FIGS. 2B,C). Data shown are mean ±S.D. (n=6 per group). *P<0.05 compared with the control mice.

FIG. 3. Cytokine gene expression. T-cells were collected from the lymph nodes of control or vaccination mice 10 days post boost and cultured in the presence of no antigen, and Der p extract (100 μg/ml) for 18 hrs. The total RNA was extracted using TRIzol reagent and RT-PCR reactions was done using cDNA with different primers specific for β-actin, IL-2, 4, 5, and interferon-γ. 1) Lymph node cells from control mice were cultured without Der p 2) in the presence of Der p (100 μg ml), 3) Lymph node cells from vaccinated mice were cultured without Der p, and 4) in the presence of Der p (100 μg/ml). A higher mRNA expression of IFN-γ in the vaccination group was detected compared with the control group.

FIG. 4. Histopathologic examination of lung. Lungs from control and experimental groups of mice were removed on day 45 after immunization. (A) Lung from control mouse (×100). (B) Lung from control mouse (×400). (C) lung from vaccination mouse (×100). (D) Lung from vaccination mouse (×400). Vaccination mice showed much less the infiltration of inflammatory cells than control mice.

Figure 5:
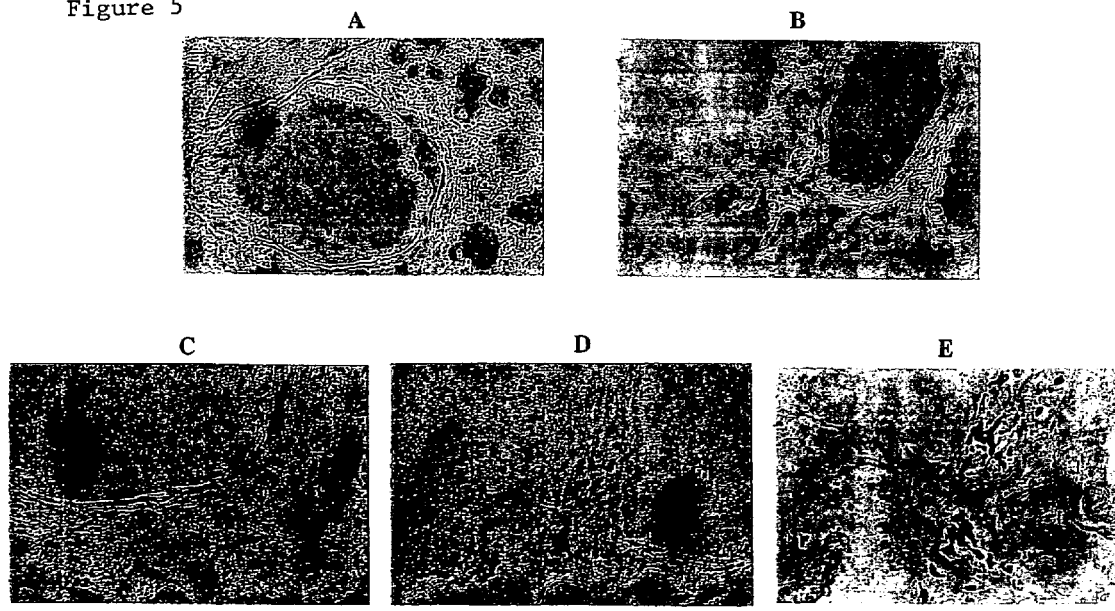
FIGS. 5A-E are photomicrographs of lung tissue from control or vaccinated mice stained for CD8+ T cells where the samples are (A) lung from a control mouse (×100), (B) lung from control mouse (×200), (C) lung from vaccination mouse (×200), and (D) bronchial wall from control mouse (×600).

FIG. 5. Immunohistochemical examination of lung. Lungs from control and vaccination group were removed on day 45 after immunization and were stained for CD8+ T-cells. (A) Lung from control mouse (×100). (B) Lung from vaccination mouse (×100). More CD8+ T-cells were observed in vaccination mice in comparing with control mice.

Example 3

Suppressive Effect on the Allergen-Induced Immunoglobulin E Production by the Naked DNA We have investigated immune responses resulting from gene immunization with plasmid DNA encoding major HDM allergen (Der p 1, 2, 3, Der f 1, 2, and 3) followed by challenges with whole HDM crude extract in mice to mimic a realistic clinical setting. We have demonstrated that gene vaccination indeed induced strong Th1 immune responses, which reduced the IgB antibody production and allergic responses against HDM.

Methods

Mice

20 BALB/c mice at the age of 6-8 weeks were purchased from Jackson Laboratory (Bar Harbor, Me.) and bred at the University of Tennessee (Memphis, Tenn.) This study was performed in accordance with the PHS Policy on Humane Care and Use of Laboratory Animals, the NIH Guide for the Care and Use of Laboratory Animal Welfare Act (7 U.S.C. et seq.); the animal use protocol was approved by the Institutional Animal Care and Use Committee (IACUC) of the University of Tennessee.

Plasmid Construction

Total mRNA was isolated from Der p and Der f HDM, respectively. By using murine leukemia virus reverse transcriptase and random hexanucleotide primers following the instructions of the Perkin Elmer Gene Amp RNA PCR kit (Perkin Elmer, Branchberg, N.J.), first-strand cDNA was generated from 1 μg of total RNA and subjected to RT-PCR. The cDNA was used in PCR with Taq polymerase and primers specific for Der p 1-3 and Der f 1-3. These primers, which cover the mature excreted region of each gene and include EcoRI and XbaI sites for cloning are summarized in Table 1. The amplified PCR products were subcloned into pcDNA3.1 eukyrotic expression vector (Invitrogen, San Diego, Calif.) and then sequenced.

DNA Preparation and Vaccination

Each plasmid construct was prepared using Maxi prep (Qiagen, Chatsworth, Calif.). Mice were vaccinated by injection with 300 μg of pcDNA3.1 blank vector in 100 μl of PBS (control group) or with 300 μg of the mixed naked DNA encoding the major HDM allergens in 100 μl of PBS (vaccination group) three times at weekly intervals into muscle (week 0, 1, and 2). To verify expression, mRNA was prepared from muscle of the injected mice, and used for RT-PCR. We found PCR products of HDM major allergen genes from experimental group mice (data not shown).

Immunization and Inhalation of Allergen to Mice

HDM crude extracts (Der p and Der 1) were dialyzed, concentrated, and dissolved in PBS buffer. HDM allergen was emulsified with an equal volume of complete Freund's adjuvant (CFA) for immunization. Three weeks after the last vaccination, mice were sensitized subcutaneously at the base of the tail with 100 μg of HDM extract in CFA (week 5). The mice were also given an intraperitoneal dose of 300 ng of purified pertussis toxin at 24 and 72 hours after first immunization. Seven days later, the mice were boosted again with the same amount of antigen in incomplete Freund's adjuvant (week 6). Mice were treated by intranasal administration with 10 μg of HDM crude extract six times at weekly intervals from boost (week 6 to 11).

Expression and Purification of Recombinant Der p 1 Peptide

Recombinant Der p 1 peptide was generated to use as an antigen. The Der p 1 gene were amplified by RT PCR with primers specific for Der p 1 (5'-CCG GAA TTC ATG GAA ACT AAC GCC TGC AGT-3' [SEQ. ID. NO:55] and 5'-TGC TCT AGA TTA GAG AAT GAC AAC ATA TGG ATA TTC-3' [SEQ. ID. NO:56]) and subcloned into pMAL-c2 (NEB, Beverly, Mass.), prokaryotic expression vector, using EcoRI and XbaI sites. Recombinant Der p 1 was expressed in *E. coli* by induction with IPTG at an O.D.$_{600}$ of 0.5 in liquid culture for 4 h at 37° C. The purification of fusion proteins was performed with amylose resin (NEB, Beverly, Mass.). Fractions containing recombinant Der p 1 of >95% purity were dialyzed against 1×PBS buffer and lyophilized until use.

Determination of IgE and HDM Specific IgG

Blood from the 6 mice in two groups was collected six times on week 0 (first vaccination), 3, 5 (first immunization), 7, 9, and 11. The HDM specific IgG levels were determined by ELISA as follows. One hundred microliters of HDM (5 μg/ml in 0.1 M carbonate buffer, pH 9.6) were dispensed in each well of a polystyrene microtiter plate (Cost, Cambridge, Mass.) and incubated overnight at 4° C. The antigen-coated plates were washed three times in 0.05% PBS-Tween 20 buffer (washing buffer) and incubated with mice sera overnight at 4° C. The plates were washed five times with washing buffer and incubated with peroxidase conjugated anti-mouse IgG antibody (Sigma, St. Louis, Mo.) overnight at 4° C. The plates were washed five times before adding citric acid-phosphate buffer (pH 5.0) containing 0.15 mg/ml of O-phenylenediamine (Sigma, St. Louis, Mo.). The color was developed at room temperature, and the reaction was stopped by 2.5 M sulfric acid. The color was measured at 492 nm (Bio-Rad, Richmond, Calif.). The total IgE level was determined by ELISA as follows. One hundred microliter of anti-mouse IgE capture mAb (clone R35-72; Pharmingen, San Diego, Calif.) were added in each well to plate and incubated overnight at 4° C. After washing, two hundred microliters of 10% fetal calf serum were incubated at room temperature for 30 min. The plates were washed five times with washing buffer and incubated with the diluted mouse serum overnight at 4° C., followed by the addition of one hundred microliter of HRP-conjugated anti-mouse IgE detection mAb (clone R35-118; Pharmingen, San Diego, Calif.) overnight at 4° C. After washing, color was developed by the same procedure as the IgG level determination. The purified mouse serum (Pharmigen, San Diego, Calif.) was used for the total IgE standard. In order to measure the HDM specific IgE, the plates were coated with 25 μg/ml HDM in 0.1 M carbonate buffer (pH 9.6) and serum samples were diluted fivefold in 10% FCS. The other procedures were the same as for the measurement of HDM-specific IgG. The level of HDM-specific IgE was referenced to the standard serum pooled from six mice that were immunized with 100 μg of HDM twice and inhaled with 10 μg of antigen six times. The standard serum was calculated as 100 ELISA units/ml.

Immunohistochemical Staining for CD4+ and CD8+ T-Cells in Lung.

The lung tissues from the experimental and control group mice were removed after the final intranasal inhalation. The tissues were fixed with periodate-lysine-paraformaldehyde solution for 24 h at 4° C. The specimens were rinsed with 0.01 M of PBS (pH 7.4), containing 10% to 20% sucrose, for 36 h at 4° C., embedded in OCT compound (Miles Laboratories Inc., Elkhart, Ind.), and immediately frozen. The lung specimen was immersed into 10% EDTA and decalcified for ten days at 4° C. Frozen sections cut at 4 to 6 μm in thickness were dehydrated and rinsed in cold PBS. The endogenous pseudoperoxidase was blocked with absolute methanol containing 0.5% hydrogen peroxide for 20 min at room temperature. The sections were treated with 10% normal goat serum in PBS to reduce the nonspecific binding. Biotin conjugated rat anti-mouse CD8 or CD4 monoclonal antibody (Pharmingen, San Diego, Calif.) diluted to 1:200 in PBS containing 0.5% bovine serum albumin was applied to the sections and incubated overnight at 4° C. After rinsing, the sections were incubated with avidin-biotin peroxidase complexes (Vectastain Elite ABC Kit, Vector Laboratories Inc., Burlingame, Calif.) for 30 min at room temperature and rinsed sufficiently with PBS. The reaction was developed with 0.02% 3,3'-diaminobenzidine in 0.05 M of Tris buffer (pH 7.6) with 0.005% hydrogen peroxidase for 7 min. The sections were dehydrated, cleared in xylene, and mounted.

Histological Examination of Lung Tissue

Mice were anesthetized with a mixture of ketalar (35 mg/ml), rompun (0.6%/ml) and atropine (0.1 mg/ml), of which 0.2 ml was injected intramuscularly. The vascular bed of the lungs was perfused with 0.01 M Phosphate-buffered saline (PBS) and then with 4% paraformaldehyde 0.1 M PBS buffers. Whole lungs were taken out and were stored in 4% paraformaldehyde for 24 h at 4° C. After fixation, these tissues were dehydrated and embedded in paraffin. Frozen sections cut at 3 μm in thickness were stained by hematoxylin and eosin. After coding, the sections were evaluated by two observers using light microscopy. The amount of inflammatory cells per section was scored using the method described by Mehlhop et al. Lungs that showed no local inflammation were scored as grade 0. Those that showed one or two centrally located microscopic foci of inflammatory infiltrate were graded as 1. In grade 2, a dense inflammatory infiltrate was seen in a perivascular and peribronchial distribution originating in the center of the lung. In grade 3, the perivascular and peribronchial infiltrates extended to the periphery of the lung.

Measuring Cytokine mRNA Expression

Mice from two groups were sacrificed 10 days postboots. The lymph nodes were removed from mice and stimulated with recombinant Der p 1 (100 μg/ml) or HDM crude extract (100 μg/ml) in vitro for 18 hrs. The cells were washed with PBS buffer and mRNAs prepared (Biotecx, Houston, Tex.). By using murine leukemia virus reverse transcriptase and random hexanucleotide primer following the instructions of the Perkin Elmer Gene Amp RNA PCR kit (Perkin Elmer, Branchberg, N.J.), first-strand cDNA was generated from 1 μg of total RNA and subjected to RT-PCR analysis. To determine the relative abundance of each cytokine mRNA expression, the amount of each cDNA for PCR was optimized by the intensity of the amplified DNA products of β-actin from each RNA. In the PCR reaction mixture, either β-actin as control primer, IL-2, IFN-γ (Clonetech, PaloAlto, Calif.), IL-4, IL-5, IL-10 at the final concentration of 0.2 M was added. The PCR condition was as follows: 200 μM of dNTP, 10 μCi [32P] dCTP, 50 μM Tris HCl (pH 9.0), 50 μM NaCl, 2 μM MgCl$_2$, 0.5 mM DTT, and two units of Taq polymerase (Perkin Elmer, Branchberg, N.J.) at a final volume of 20 μl. A negative control reaction was run with each sample to verify that no PCR bands appeared in the absence of template. The optimal amplification conditions were as follows: 45 s at 94° C. for denaturation, 45 s at 67° C. for annealing, and 1 min at 72° C. for elongation and the PCR cycles were 30. The amplified DNAs of β-actin, IFN-γ, IL-2, IL-4, IL-5, and IL-10 had sizes of 540, 365, 413, 354, 349, and 455 base-pairs, respectively. The gel was dried on Whatman 3M paper and exposed to Kodak XAR film. In each electrophoresis run, intra- and inter-gel staining homogeneity was confirmed by staining intensity of molecular weight markers at both ends of the gels. In general, amplification kinetics were monitored for each PCR run by examining aliquots of the products on the gel. Amounts of the PCR products were compared during the cycles where the amplification did not reach saturation.

Statistical Analysis

Immunoglobulin response data were analyzed by Student's paired t test for comparisons between the control and experimental group. Histological grades were analyzed using a non-parametric Wilcoxon test. Data was expressed as mean ±SD. A P value<0.05 was considered significant.

Results

Downregulation of Der p-Specific IgE Antibody Production by Gene Vaccination.

Figure 3C:
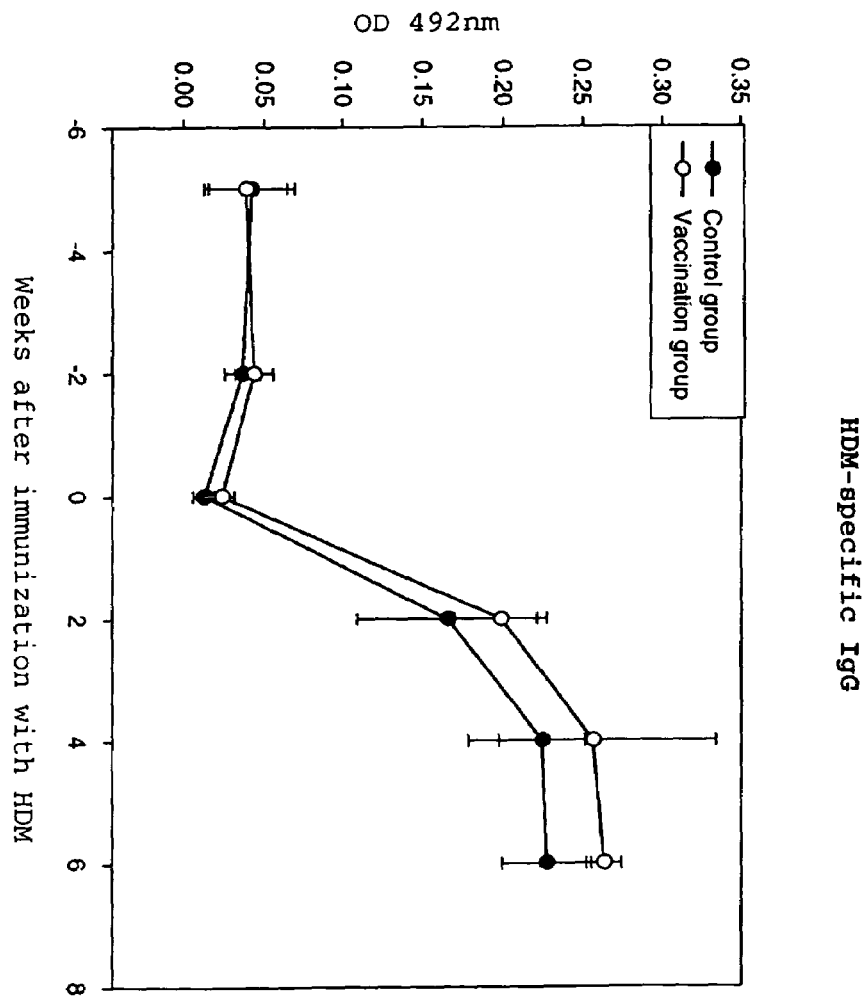

To examine the immune response, we checked levels of the IgG and IgE antibody productions by ELISA (FIG. 3). The gene vaccination with the major HDM allergen genes, Der p 1, 2, 3, Der f 1, 2, and 3, showed about 70% inhibition of HDM-specific IgE and more than 70% inhibition of total IgE as compared with the control group after 6 weeks immunization. Thus, genetic vaccination could inhibit an in vivo allergen-specific IgE synthesis efficiently even though HDM-specific IgG antibody production of both groups were at almost the same level (FIG. 3C).

Histological and Immunohistochemical Study

To examine whether the genetic vaccination has an affect on the cellular response of lung or not, we stained the lung at the end of the experiment by histological and immunohistochemical methods. The lungs from the control group (mean grade 1.64±0.52) showed much greater infiltration of inflammatory cells in the submucosa of airways than that of the vaccination group (mean grade 0.68±0.48). Eosinophils were also detected in the lungs of the control mice (FIGS. 4 and 5). In the immunohistochemical stain for CD4+ and CD8+, T-cells showed that more CD8+ T-cells infiltrated the submucosa and mucosa of the airway of the lung from the vaccination group as compared with the control group (FIGS. 4 and 5). However, in the stain for the CD4+ T-cells showed no difference between the two groups. The results suggested that the genetic vaccination also affect the cellular response and the CD8+, T-cells of the vaccination were capable of protecting against a subsequent allergenic challenge.

Cytokine Gene Expression by Antigen Stimulation In Vivo

To determine whether the Th1 or Th2 cytokines are involved in the effect of genetic vaccination, T-cells were harvested from lymph nodes of the two groups of mice and stimulated with recombinant Der p 1 or HDM crude extract in vivo. A higher mRNA expression of IFN-γ in the vaccination group was detected compared with the control group. However in the mRNA expression of IL-2, 4, 5, and 10 of both groups were similar. These data indicate that the vaccinations with HDM major genes induced a strong Th1 cytokine (IFN-γ) gene expression in the lymph node.

Discussion

Diseases such as allergic asthma, rhinitis, and atopic dermatitis are all characterized by elevated levels of serum IgE. Total and specific IgE positivity also showed a close relationship with clinical symptoms of atopic allergy.[15] A variety of approaches targeting the suppression of IgE have been proposed using synthetic peptides as a T-cell vaccine. However, the synthetic peptides were poor immunogens and were needed at higher levels than the amount derived intracelluarly from processed antigens. Recently Hsu et al.[10] showed that gene immunization of rats with plasmid encoding Der p 5 prevent induction of IgE synthesis. These data suggest that pDNA immunization with a plasmid containing the gene for the minor HDM allergen Der p 5 may induce Th1 immune responses to the encoded antigens. The Der p 5 allergen reacts with about only 40% of allergic sera, but the Der p 1 and 2 allergens react with about 80% of allergic sera. We have analyzed the effects of gene vaccination with plasmid encoding major 6 HDM allergens (Der p 1, 2, and 3, Der f 1, 2, and 3) in allergic responses to whole HDM crude extract. Our results showed about 50% inhibition of HDM-specific IgE and more than 70% inhibition of total IgE at week at the end of the study (FIGS. 3a and b). Thus, this result suggested that gene immunization with a plasmid encoding the major HDM antigen can also induced inhibition of IgE synthesis. Animal models have established that Th2 responses are mediated by T helper cells that secret cytokines such as IL-4, IL-5 and IL-10 that induce antibody production in B cells, including above all, the formation of IgE which plays a central role in allergic responses. IFN-γ the Th1 cytokine responsible for the inhibition of IL-4-mediated IgE responses and promotes the formation of IgG2a. Previous reports showed that protein immunization induced a TH2 response, as shown by IgG1 and IgE antibody formation and IL-4 and IL-5-secreting T-cells. In contrast, gene immunization with plasmid DNA induced a Th1 response with IgG2a antibody production and IFN-γ secreting T-cells. Genetic vaccination in many infectious disease, and allergic disease have an enhanced Th1 response for preventing several diseases. Our gene vaccination data showed that the mRNA expression of IFN-γ in the lymph node from pDNA encoding the HDM allergens Der p 1, 2, 3, & and Der f 1, 2, 3 gene increased more than that from the control group. This data suggested that the genetic immunization might induce Th1 immune response to the encoded antigen or allergen. After genetic immunization, the Th1 response dominated over the TH2 response and downregulates preexisting IgE antibody formation. Our experiment suggested that genetic immunization might suppress IgE production by the inducing the TH1 response from T helper cells.

Allergic asthma is characterized as a chronic inflammatory disease of the bronchi and it is well established that a variety of cells including mast cells, eosinophils and lymphocytes play a role in this process. After an inhalation challenge, the inflammatory cells migrate from the peripheral blood to the site of inflammation in the bronchial mucosa and bronchoalveolar fluid expressing predominantly Th2-type cytokines. Our histological study showed that gene vaccination induced the reduction of infiltration of inflammatory cells in lung tissues (FIG. 4). This result suggested that the change in the function of T-cells might cause the reduction of the inflammatory cells in bronchial mucosa. This data indicated that gene immunization affects not only humoal immune responses but also cellular responses. T lymphocytes have been suggested to play a key role in orchestrating the interaction of the participating cells since they are able to release an array of cytokines which can attract, prime and activate other cell types. A successful outcome of immunotherapy has been associated with the development of suppressor T-cells, which can downregulate the allergic response. Recent data have also revealed that functionally distinct subsets of CD8+ T-cells may play an important regulatory role in IgE production. However, Manickan et al. showed that the mechanism of genetic immunization was principally by CD4+ T-cells, and not by CD8+ T-cells. Recently Lee et al. reported that both CD4+ and CD8+ subsets of T-cells from mice immunized with plasmid DNA can suppress IgE antibody production by affecting the primary response and/or by propagating the Th1 memory response in a passive cell transfer system. Our immunohistochemical study showed that more CD8+ T-cells were detected in the lung of the vaccinated group than that of the control group (FIG. 5). Peptides derived from extracellular molecules are presented to CD4+ T-cells by MHC class II molecules normally generated by antigen-presenting cells,[36] whereas peptides derived from cytosolic proteins are generally presented to CD8+ T-cells by major histocompatibility complex (MHC) class 1 molecules which are expressed on virtually all somatic cells. We injected the mixed naked DNA into muscle of BALB/c mice. Our Results suggested that such endogenous production of an allergenic protein might be a useful means to induce regulatory CD8+ T-cells capable of conferring protection against a subsequent allergenic challenge. Our represented results here showed that vaccination with plasmid DNA encoding specific allergen genes in an animal model provided an efficient clinical method for modulation allergic responses.

TABLE 6

Oligonucleotides used for Der p 1-3 and Der f 1-3 in this study

| Molecule | Primer Sequence (5' to 3') |
|---|---|
| Der p 1 | 5'-CCG GAA TTC GCC GCC ACC ATG GAA ACT AAC GCC TGC AGT ATC AAT GGA-3' [SEQ. ID. NO:21] |
| | 5'-TGC TCT AGA TTA GAG AAT GAC AAC ATA TGG ATA TTC-3' [SEQ. ID. NO:22] |
| Der p 2 | 5'-CCG GAA TTC GCC GCC ACC ATG GAT CAA GTC GAT GTC AAA GAT TGT GCC-3' [SEQ. ID. NO:23] |
| | 5'-TGC TCT AGA TTA ATC GCG GAT TTT AGC ATG AGT AGC AAT-3' [SEQ. ID. NO:24] |

TABLE 6-continued

Oligonucleotides used for Der p 1-3 and Der f 1-3 in this study

| Molecule | Primer Sequence (5' to 3') |
|---|---|
| Der p 3 | 5'-CCG AAA TTC GCC GCC ACC ATG ATT GTT GGT GGT GAA AAA GCA TTA GCTG-3' [SEQ. ID. NO:25] |
| | 5'-TGC TCT AGA TTA CTG TGA ACG TTT TGA TTC AAT CCA ATC GATA-3' [SEQ. ID. NO:26] |
| Der f 1 | 5'-CCG GAA TTC GCC GCC ACC ATG GAA ACA AGC GCT TGC CGT ATC AAT TCG-3' [SEQ. ID. NO:27] |
| | 5'-TGC TCT AGA TTA GAG GTT GTT TCC GGC TTG GAA ATA TCC G-3' [SEQ. ID. NO:28] |
| Der f 2 | 5'-CCG GAA TTC GCC GCC ACC ATG GAT CAAA GTC GAT GTT AAA GAT TGT GCC-3' [SEQ. ID. NO:29] |
| | 5'-TGC TCT AGA TTA ATC ACG GAT TTT ACC ATG GGT AGC AAT-3' [SEQ. ID. NO:30] |
| Der f 3 | 5'-CCG GAA TTC GCC GCC ACC ATG ATT GTT GGT GGT GTG AAA GCA CAA GCC-3' [SEQ. ID. NO:31] |
| | 5'-TGC TCT AGA TTA CTG TGA ACG TTT TGA TTC AAT CCA ATC GAC-3' [SEQ. ID. NO:32] |

TABLE 7

Oligonucleotides used for cytokine mRNA expression in this study

| Molecules | Primer Sequence (5' to 3') | Product Size |
|---|---|---|
| β-actin | 5'-GTG GGC CGC TCT AGG CAC CAA-3' [SEQ. ID. NO:33] | 540 bp |
| | 5'-CTC TTT GAT GTC ACG CAC GAT TTC-3' [SEQ. ID. NO:34] | |
| IL-2 | 5'-TTCAAGCTCCACTTCAAGCTCTACAGCGGAAG-3' [SEQ. ID. NO:35] | 413 bp |
| | 5'-GACAGAAGGCTATCCATCTCCTCAGAAAGTCC-3' [SEQ. ID. NO:36] | |
| IFN-γ | 5'-TGCATCTTGGCTTTGCAGCTCTTCCTCATGGC-3' [SEQ. ID. NO:37] | 365 bp |
| | 5'-TGGACCTGTGGGTTGTTGACCTCAAACTTGGC-3' [SEQ. ID. NO:38] | |
| IL-4 | 5'-CAG CTA GTT GTC ATC CTG CTC TTC-3' [SEQ. ID. NO:39] | 357 bp |
| | 5'-GTG ATG TGG ACT TGG ACT CAT TCA TGG-3' [SEQ. ID. NO:40] | |
| IL-5 | 5'-TGT CTG GGC CAC TGC CAT GGA GAT TC-3' [SEQ. ID. NO:41] | 424 bp |
| | 5'-CCA TTG CCC ACT CTG TACT CA TCA CAC-3' [SEQ. ID. NO:42] | |
| IL-10 | 5'-ATG CAG GAC TTT AAG GGT TACT TG GGT-3' [SEQ. ID. NO:43] | 455 bp |
| | 5'-ATT TCG GAG AGA GGT ACA AAC GAG G-3' [SEQ. ID. NO:44] | |

Figure Legend

FIG. 3. Effect of vaccination on the allergen induced immuoglobulin production. The total IgE antibody response (A), and the HDM-specific IgE antibody response (B), and changes of HDM-specific IgG antibody response (C), of BALB/c mice after immunization of whole HDM crude extract. Data shown are means ±SD (n=6 per group). *P<0.05 compared with the control group.

FIG. 4. Histopathologic Examination of Lung.

Lungs from control and experimental groups of mice were removed on day 45 after immunization. (A) Lung from control mouse (×100). (B) Lung from control mouse (×200). (C) Lung from vaccination mouse (×200). (D) Bronchial wall from control mouse (×600). Eosinophils and many inflammatory cells were observed in control group. Vaccination mice showed much less infiltration of inflammatory cells than control mice.

FIG. 5. Immunohistochemical Examination of Lung.

Lungs from control and vaccination group were removed on day 45 after immunization and were stained for CD8+ T-cells. (A) Lung from control mouse (×100). (8) Lung from vaccination mouse (×100). (C) Lung from control mouse (×200). (D) Lung from vaccination mouse (×200). (E). Bronchial wall from vaccination mouse (×400). More CD8+ T-cells were observed in vaccination mouse.

T-cells were collected from the lymph nodes of control or vaccination mice 10 days post boost and cultured in the presence of no antigen (−), recombinant Der p 1 (100 µg/ml), and HDM crude extract (100 µg/ml) for 18 h. The total RNA was extracted using TRIzol reagent and RT-PCR reactions were doing using cDNA with different primers specific for β-actin, IL-2, 4, 5, 10 and interferon-γ.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

1. Platts-Mills, T. A. E., and Chapman. M. D., Dust mites: immunology, allergic disease, and environmental control. J. Allergy Clin. Immunol. 1987; 80:755-75.
2. International workshop report. Dust mite allergens and asthma: a world wide problem. WHO Bulletin 1988; 66:769-80.
3. Ulmer, J. B., Donnelly, J. J, Parker, S. E., Rhodes, G. H., Felgner, P. L., Dwarki, V. J., Gromkowski, S. H., Deck, R. R., DeWitt, C. M., Friedman, A., Hawe, L. A., Leander, K. R., Martinez, D., Perry, H. C., Shiver, J. W., Montgomery, D. L., and Liu, M. A., Heterologous protection against influenza by infection of DNA encoding a viral protein. Science 1993; 259:1745-49.
4. Wang, B., Ugen, K. E., Srikantan, V., Agadjanyan, M. G., Dang, K., Refaeli, Y., Sato, A. I., Boyer, J., Williams, W. V., and Weiner, D. B., Gene inoculation generates immune responses against human immunodeficiency virus type 1. Proc. Natl. Acad. Sci. USA 1993; 90:4156-60.
5. Raz, E., Carson, D. A., Parker, S. E., Par, T. B., Abai, A. M., Aichinger, G., Gromkowski, S. H., Lew, D., Uankauckas, M. A., Baird, S. M., and Rhodes, G H., Intradermal gene immunization: The possible role of DNA uptake in the induction of cellular immunity to viruses. Proc. Natl. Acad. Sci. USA 1994; 91:9519-23.
6. Wolff, J. A., Ludtke, J. J., Acsadi, G., Williams, P., and Jani, A, Long persistence of plasmid DNA and foreign gene expression in mouse muscle. Hum. Mol. Gen. 1992; 1:363-

39. 7. Hsu, C. H., Chua, K. Y., Tao, M. H., Lai, Y. L., Wu, H. D., Huang, S. K., and Hsieh, K. H., Immunoprophylaxis of allergen-induced immunoglobulin E synthesis and airway hyperresponsiveness in vitro by genetic immunization. Nature Med. 1996; 2:540-44.
8. Slater, J. E., Zhang, Y. J., Arthur-Smith, A. A., Colberg-Poley, A. A., DNA vaccine inhibits IgE responses to the latex allergen Hev b 5 in mice. J. Allergy Clin. Immunol. 1997; 99:s504.
9. Broide, D., Orozco, E. M., Roman, M., Carton, D. A., and Raz, E., Intradermal gene vaccination down-regulates both arms of the allergic response. J. Allergy Clin. Immunol. 1997; 99:s 129.
10. Raz, E., Tighe, H., Sato, Y., Corr, M. P., Dudler, J. A., Roman, M., Swain, S. L., Spiegelberg, H. L., and Carson, D. A., Preferential induction of a TH1 response and inhibition of specific IgE antibody formation by plasmid DNA immunization. Proc. Natl. Acad. U.S.A. 1996; 93:5141-45.
11. Cheng, K. C, Lee, K. M., Krug, M. S., Watanabe, T., Suzuki, M., Choe, I. S., and Yoo, T. J., House dust mite-induced sensitivity in mice. J. Allergy Clin. Immunol. 1998; 101:51-59.
12. Enander, I., Ahlstedt, S., and Nygren, H., Mononuclear cells, mast cells and mucous cells as part of the delayed hypersensitivity response to aerosolized antigen in mice. Immunol. 1984; 51:661-68.
13. Hessel, E. M., Van Oosterhout, A. J. M., Hofstra, C. L., De Bie, J. J., Garssen, J., Van Loveren, H., Verheyen, A. K. C. P., Savelkoul, H. F. J., and Nijkamp, F. P., Bronchoconstriction and airway hyperresponsiveness after ovalbumin inhalation in sensitized mice. European Journal of Phamacology Environmental Toxicology and Phamacology 1995; Section 293:401-12.
14. Droste, J. H., Kerkhof, M., de Monchy, Jan G. R., Schouten, Jan P., Rijcken, B., and Dutch ECRHS group: Association of skin test reactivity, specific IgE, total IgE, and eosinophils with nasal symptoms in a community-based population study. J. Allergy Clin. Immunol. 1996; 97:922-32.
15. Yssel, H., Johnson, K. E., Schneider, P. V., Wideman, J., Terr, A., Kasteein, R., and de Vries, J. E, activation-inducing epitopes of the house dust mite allergen Der p 1. Proliferation and lymphokine production patterns by Der p 1-specific CD+4 T-cell clones. J. Immunol. 1992; 148, 738-45.
16. Higgins, J. A., Lamb, J. R., March, S. G. E., Hayball, J. D., Rosen-Bronson, S., Bodmer, J. G., and O'Hehir, R. E., Peptide-induced nonresponsiveness of HLA-DP restricted human T-cells reactive with *Dermatophagoides* spp. (house dust mite). J. Allergey Clin Immunol. 1992; 90:749-56.
17. Bot, A., Rot, S., Karjalainen, K., and Bona, C., Kinetics of generation and persistence on membrane class II molecules of a viral peptide expressed on foreign and self proteins. J. Immunol. 1996; 157(8):3436-42.
18. Demotz, S., Grey, H. M., and Sette, A., The minimal number of class II MHC-antigen complexes needed for T-cell activation. Science 1990; 249(4972): 1028-30. 19. Van der Zee, J. S., Van Swieten, P., Janse, H. M., and Aalberse, R C., Skin tests and histamine release with P1-depleted *Dermatophagoides pteronyssinus* body extracts and purified P1. J. Allergy Clin. Immunol. 1988; 81:884-951.
20. Lin, K. L., Hsieh, K. H., Thomas, W. R., Chiang, B. L., and Chua, K Y., Allergens, IgE, Mediators, inflammatory mechanisms. Characterization of Der p 5 allergen, cDNA analysis, and IgE-mediated reactivity to the recombinant protein. J. Allergy Clin. Immunol. 1994; 94:989-96.
21. Singer, G. G., and Abbas, A. K., The Fas antigen is involved in peripheral but not thymic deletion of T lymphocytes in T-cell receptor transgenic mice. Immunity 1994; 1:365-71.
22. Chen, Y., Inobe, J., Marks, R., Gonnella, P., Kuchroo, V. K., and Weiner, H. L., Peripheral deletion of antigen-reactive T-cells in oral tolerance. Nature 1995; 376: 177-80.
23. Tighe, H., Corr, M., Roman, M., and Raz, E., Gene vaccination: plasmid DNA is more than just a blueprint. Immunol. Today 1998; 19(2):89-97.
24. Mosmann, T. R., and Coffman, R. L., TH1 and TH2 cells: different patterns of lymphokine secretion lead to different functional properties. Annu. Rev. Immunol. 1989; 7:145-73.
25. Finkelman, F. D., Katona, I. M., Urban, J. F. Jr., Holmes, J., Ohara, J., Tung, A. S., Sample, J. V. G., and Paul, W. E., IL-4 required to generate and sustain in vivo IgE responses. J. Immunol. 1988; 141:2335-41.
26. Snapper, C. M., and Paul, W. E., Interferon-γ and B cell stimulatory factor-1 reciprocally regulate Ig isotype production. Science 1987; 236:944-47.
27. Lee D. J., Tighe, H., Corr, J. A., Roman, M., Carson, D. A., Spiegelberg, H. L., and Raz, E., Inhibition of IgE antibody formation by plasmid DNA immunization is mediated by both CD4+ and CD8+ T-cells. Int. Arch. Allergy Immunol. 1997; 113:227-30.
28. Coffman, R. L., Ohara, J., Bond, M. W., Carty, J., Zlotnik, A. and Paul, W. E., B cell stimulatory factor-1 enhances the IgE response of lipopolysaccharide-activated B cells. J. Immunol. 1986; 136(12):4538-41.
29. Krug N., Tshernig, T., Holgate, S., and Pabst, R., How do lymphocytes get into the asthmatic airways? Lymphocyte traffic into and within the lung in asthma. Clini. Experi. Allergy 1998; 28:10-18.
30. Ying, S., Durham, S. R., Cirrogan, C. J., Hamid, Q., and Kay, A. B., Phenotype of cells expressing mRNA for Th2-type (interleukin 4 and interleukin 5) and Th1-type (interleukin 2 and interferon) cytokines in bronchoalveolar lavage and bronchial biopsies from atopic asthmatic and normal control subjects. Am. J. Respir. Cell Mol. Biol. 1995; 12:477-87.
31. Humbert, M., Durham, S. R., Ying, S., Kimmitt, P., Barkans, J., Assoufi, B., Pfister, R., Menz, G., Robinson, D. S., Kay, A. B., and Corrigan, C. J., IL-4 and IL-5 mRNA and protein in bronchial biopsies from patients with atopic and nonatopic asthama: evidence against 'intrinsic' asthma being a distinct immunopathologic entity. Am, J, Respir, Crit, Care Med, 1996; 154:1497-504.
32. Hsieh, K. H., Changes of lymphoproliferative responses of T-cell subsets to allergen and mitogen after hyposensitization in asthmatic children. J. Allergy Clin. Immunol. 1984; 74:34-40.
33. Hsieh, K. H., Lue, K. H., and Chiang, C. F., Immunological changes after hyposensitization in house-dust-sensitive asthmatic children. J. Asthma 1987; 24:19-27.
34. Mehlhop et al., A murine model of allergic rhinitis: studies on the role of IgE in pathogenesis and analysis of the eosinophil influx elicited by allergen and eotaxin. J. Allergy Clin. Immunol. 1998; 102(1):65-74
35. Manickan et al., Genetic immunization again s herpes simplex virus: Protection is mediated by CD4+ T lymphocytes. J. Immunol. 1995; 155:259-265.

The invention claimed is:

1. A method comprising administering to a human, a composition comprising a pharmaceutically acceptable carrier and an isolated, naked DNA comprising a DNA fragment encoding a polypeptide consisting essentially of a portion of an immunogenic dust mite antigen to a human, wherein said DNA fragment is amplified by a primer pair selected from the group consisting of SEQ ID NO:45 and SEQ ID NO:46 for Der p 1, SEQ ID NO:47 and SEQ ID NO:48 for Der p 1, SEQ ID NO:49 and SEQ ID NO:50 for Der p 2, SEQ ID NO: 51 and SEQ ID NO:52 for Der p 2, SEQ ID NO: 53 and SEQ ID NO:54 for Der p 2, SEQ ID NO:1 and SEQ ID NO:2 for Der p 1, SEQ ID NO:3 and SEQ ID NO:4 for Der p 1, SEQ ID NO:5 and SEQ ID NO:6 for Der p 1 SEQ ID NO:7 and SEQ ID NO:8 for Der p 2, SEQ ID NO:9 and SEQ ID NO:10 for Der p 2, SEQ ID NO:21 and SEQ ID NO:22 for Der p 1 SEQ ID NO:23 and SEQ ID NO:24 for Der p 2, SEQ ID NO:25 and SEQ ID NO:26 for Der p 3, SEQ ID NO:27 and SEQ ID NO:28 for Der f 1, SEQ ID NO:29 and SEQ ID NO:30 for Der f 2, and SEQ ID NO:31 and SEQ ID NO:32 for Der f 3.

2. The method of claim 1 wherein the DNA is plasmid DNA.

3. The method of claim 1 wherein the composition is administered intramuscularly.

4. The method of claim 1 wherein the composition is administered to a human having an allergic reaction to dust mites.

5. The method of claim 1, wherein said portion of an immunogenic dust mite antigen is a portion of Der p 1 amplified by a primer pair selected from the group consisting of SEQ ID NO:45 and SEQ ID NO:46, SEQ ID NO:47 and SEQ ID NO:48, SEQ ID NO:1 and SEQ ID NO:2, SEQ ID NO:3 and SEQ ID NO:4, SEQ ID NO:5 and SEQ ID NO:6, and SEQ ID NO:21 and SEQ ID NO:22.

6. The method of claim 1, wherein said portion of an immunogenic dust mite antigen is a portion of Der p 2 amplified by a primer pair selected from the group consisting of SEQ ID NO:49 and SEQ ID NO:50, SEQ ID NO: 51 and SEQ ID NO:52, SEQ ID NO: 53 and SEQ ID NO:54, SEQ ID NO:7 and SEQ ID NO:8, SEQ ID NO:9 and SEQ ID NO:10, and SEQ ID NO:23 and SEQ ID NO:24.

7. A composition comprising a pharmaceutically acceptable carrier and an isolated naked DNA encoding a portion of an immunogenic dust mite antigen, wherein said portion of an immunogenic dust mite antigen is a portion of Der p 3 amplified by primers SEQ ID NO:25 and SEQ ID NO:26.

8. A composition comprising a pharmaceutically acceptable carrier and an isolated naked DNA encoding a portion of an immunogenic dust mite antigen, wherein said portion of an immunogenic dust mite antigen is a portion of Der f 3 amplified by primers SEQ ID NO:31 and SEQ ID NO:32.

* * * * *